Figure 1:
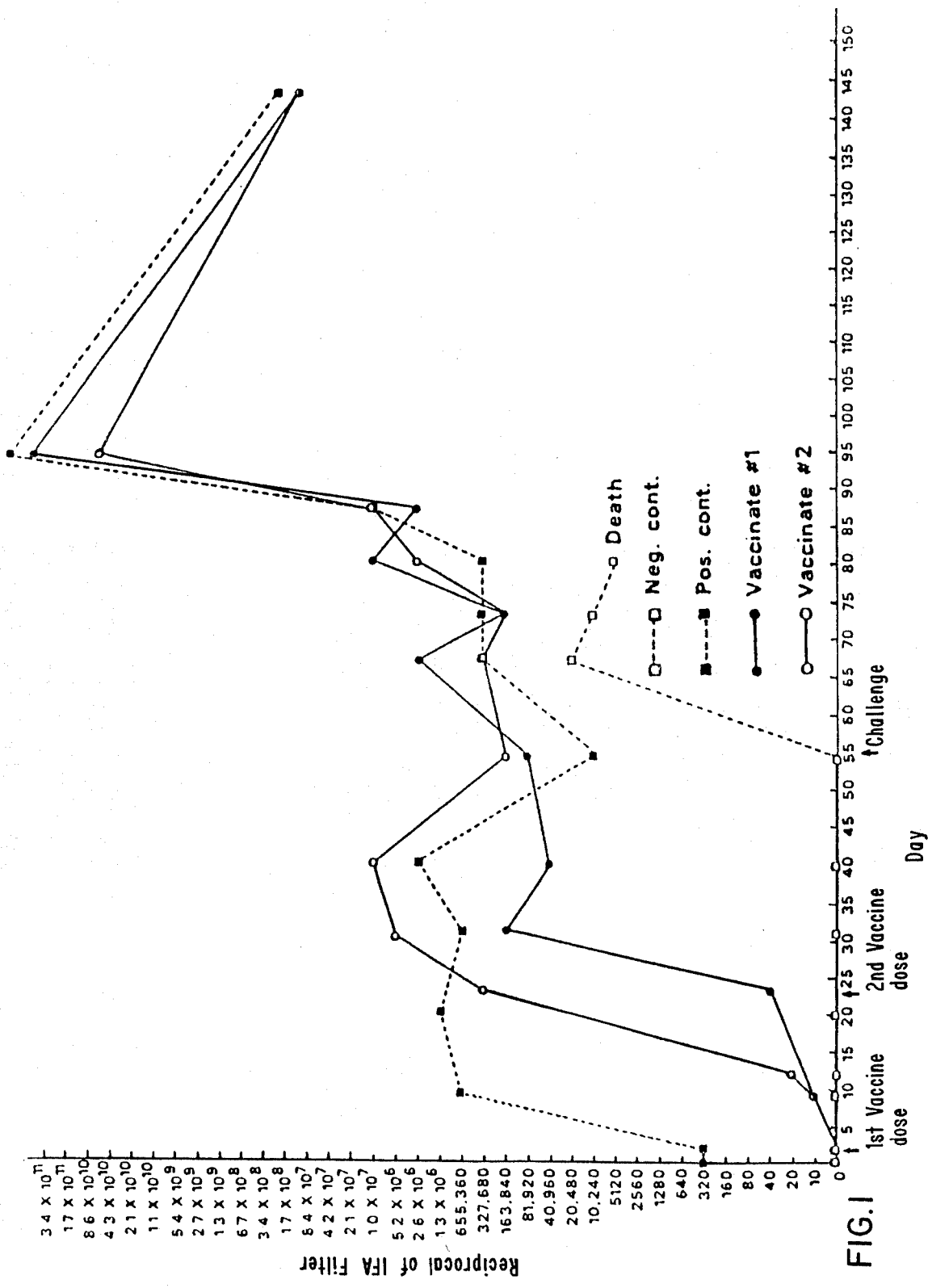

United States Patent [19]

Ristic et al.

[11] Patent Number: 4,767,622

[45] Date of Patent: Aug. 30, 1988

[54] METHOD AND MATERIALS FOR DEVELOPMENT OF IMMUNOLOGICAL RESPONSES PROTECTIVE AGAINST MALARIAL INFECTION

[75] Inventors: Miodrag Ristic; Mary L. Chilbert, both of Urbana, Ill.

[73] Assignee: University of Illinois, Urbana, Ill.

[21] Appl. No.: 524,919

[22] Filed: Aug. 19, 1983

[51] Int. Cl.$^4$ .................. A61K 39/00; C12P 21/00; C07G 7/00

[52] U.S. Cl. .................. 424/88; 530/350; 530/403; 530/822; 435/68; 435/70

[58] Field of Search .................. 424/85, 88, 195, 92; 435/2, 243, 68, 70, 240, 241; 260/112 R; 530/350, 403, 822

[56] References Cited

U.S. PATENT DOCUMENTS

| | | | |
|---|---|---|---|
| 4,466,917 | 8/1984 | Nussenzweig et al. | 260/112 R |
| 4,596,707 | 6/1986 | Ristic et al. | 424/88 |
| 4,643,896 | 2/1987 | Asakura et al. | 424/88 |
| 4,693,997 | 9/1987 | McCutchan et al. | 514/15 |

FOREIGN PATENT DOCUMENTS

0044188 1/1982 European Pat. Off. .............. 435/68
2099300 12/1982 United Kingdom .

OTHER PUBLICATIONS

Grothaus et al., *Infection and Immunity*, vol. 28(1), Apr. 1980, pp. 245–253, "Isolation of a Soluble Component of *Plasmodium berghei* . . . Rats".

Holder et al., *Nature*, vol. 294, Nov. 26, 1981, pp. 361–363, "Immunization Against Blood-Stage Rodent Malaria Using Purified Parasite Antigens".

Weiss et al., *Exp. Parasitol.*, vol. 51, 1981, pp. 400–407, "*Plasmodium falciparum*: Assay in vitro for Inhibitors of Merozoitic Penetration of Erythrocytes".

Siddiqui et al., *Nature*, vol. 289, Jan. 1/8, 1981, "Use of a Synthetic Adjuvant in an Effective Immunization of Monkeys against Malaria", pp. 64–66.

Tungery et al., *Proc. Natl. Acad. Sci.*, Feb. 1983, vol. 80, pp. 1018–1022, "A Lectin-Like Receptor is Involved in the Invasion of Erythrocytes by *Plasmodium falciparum*".

Perrin et al., *Trans. Roy. Soc. Trop. Med. Hyg.*, vol. 75(1), 1981, "Characterization of Antigens from Erythroytic Stages of *Plasmodium falciparum* Reacting with Immune Human Sera".

Wallach et al., *J. Mol. Med.*, vol. 2, pp. 119–136, 1977.

McColm et al., *Parasite Imm.*, vol. 4, pp. 337–345.

Perrin et al., *Chem. Abst.*, vol. 94, No. 206968w, "Characterization of Antigens . . . Immune Serums".

*Science*, vol. 193, Aug. 20, 1976, pp. 673–675, Trager, William et al., "Human Malaria Parasites in Continuous Culture".

*Primary Examiner*—Thomas G. Wiseman
*Assistant Examiner*—Robin Lyn Tiejkin
*Attorney, Agent, or Firm*—Marshall, O'Toole, Gerstein, Murray & Bicknell

[57] ABSTRACT

Disclosed are vaccine compositions for use in developing protective immunity against infection by Plasmodium parasites. Soluble proteinaceous immunogens are isolated from the fluid culture medium of in vitro propagated plasmodial species parasites (e.g., *P. falciparum*) in mammalian erythrocyte culture supernatant or from washes, including hypotonic washes, of cultured erythrocytes parasitized by plasmodium. Immunogens so obtained have molecular weights in the range from about 35,000 daltons to about 85,000 daltons. Two principal immunogens of the invention have molecular weights of about 42,000 and 54,000 daltons, respectively. The water soluble immunogens are administered in a suitable carrier such as isotonic salt solution and in combination with a suitable adjuvant such as saponin or, preferably, aluminum hydroxide. Upon administration to vertebrate animals susceptible to plasmodial infection, vaccines according to the invention provoke immune responses protective against morbidity and mortality caused by, e.g., *P. falciparum* infection. Disclosed also are procedures for optimization of large scale plasmodial parasite growth in human erythrocyte cultures with accompanying development of late erythrocytic stage parasites in large numbers and optimization of isolatable quantities of culture medium supernatant and wash-derived immunogens.

6 Claims, 9 Drawing Sheets

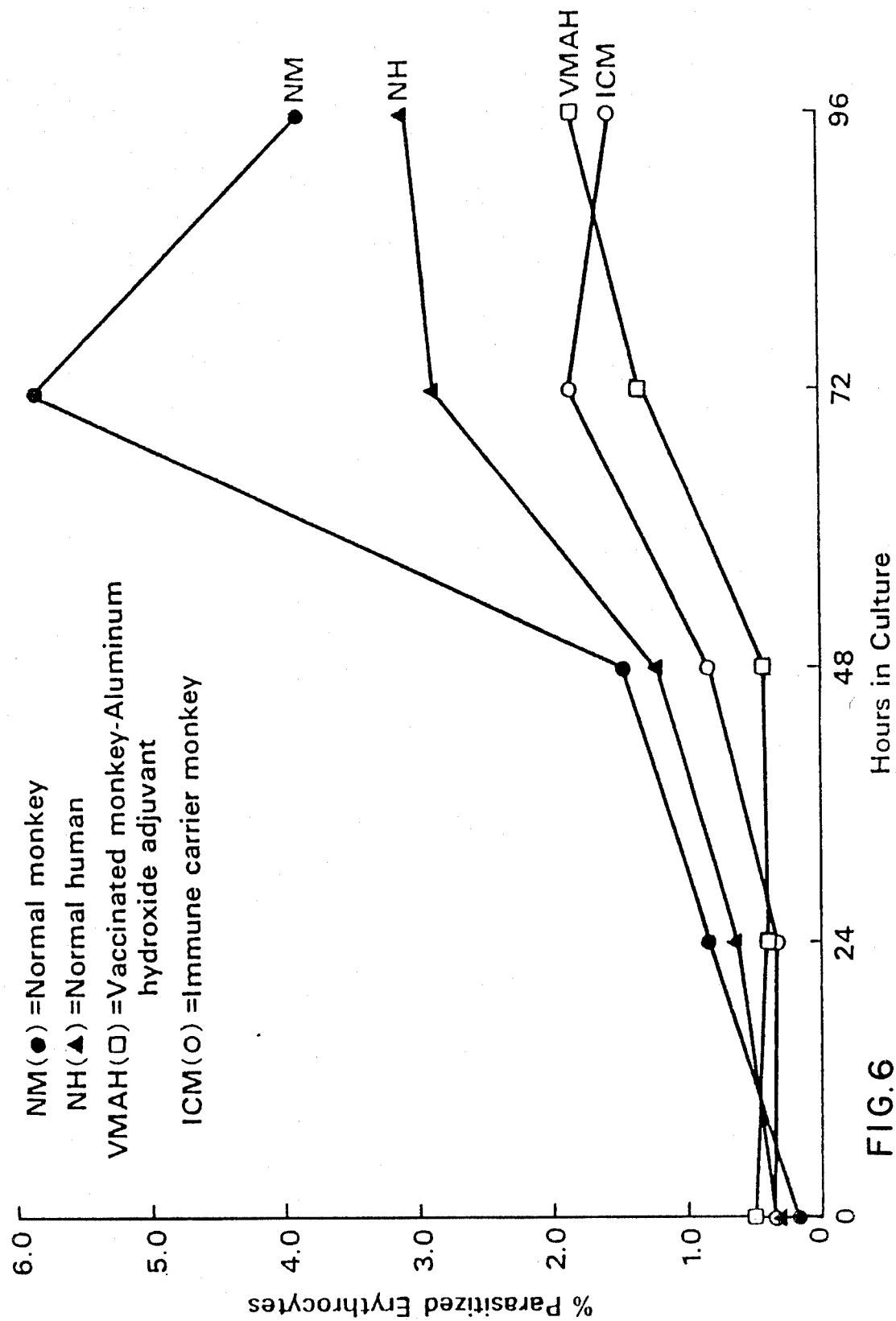

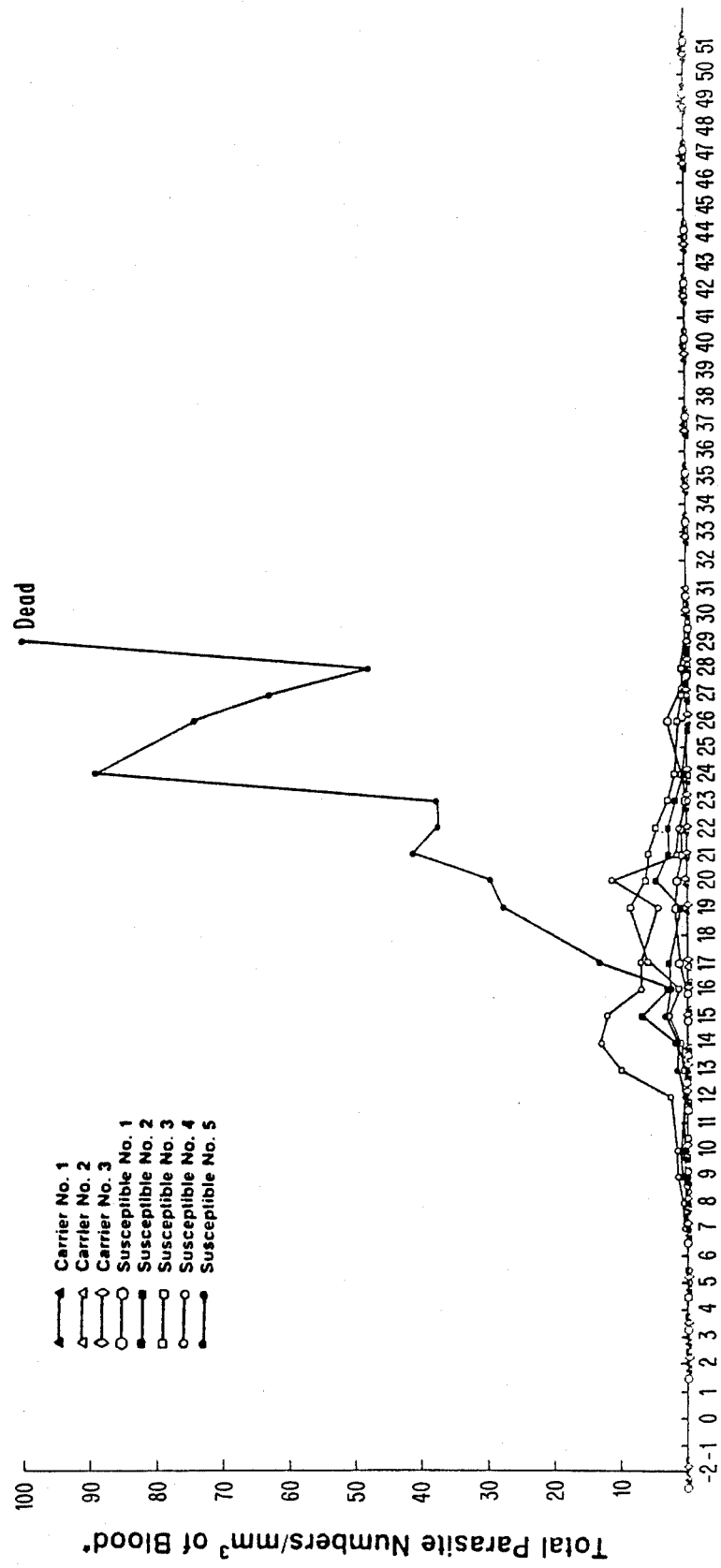

METHOD AND MATERIALS FOR DEVELOPMENT OF IMMUNOLOGICAL RESPONSES PROTECTIVE AGAINST MALARIAL INFECTION

BACKGROUND

The present invention relates generally to methods and materials useful in development of immunological responses protective against malarial infection in susceptible vertebrates, including humans.

Human malaria is caused by species of parasitic organisms of the genus *Plasmodium*. It is transmitted by mosquitoes which ingest sexual forms of the parasite in blood meals. Sporozoite forms of the parasite develop in the mosquito and are transmitted to new host individuals bitten by the insect. In the new host, the sporozoite parasites develop and multiply in an "exoerythrocytic" cycle in the liver without inducing clinical symptoms. The merozoite forms resulting from exoerythrocytic propagation then invade host erythrocytes, initiating an "erythrocytic" cycle of development and prompting the clinical symptoms of malaria. Destruction of red blood cells occurs on a 48-hour cycle with *P.vivax*, *P.ovale* and *P.falciparum*, and every 72 hours with *P.malariae*. Characteristic chills-fever-sweat malarial symptoms follow this cyclic pattern, being induced by rupture of infected red blood cells by the mature asexual forms (schizonts), releasing merozoites that quickly invade new red cells. In contrast to the exoerythrocytic stage, erythrocytic merozoites induce an array of humoral responses in the host, as demonstrated by appearance of blood serum antibodies detectable by complement fixation, precipitation, agglutination, and fluorescent antibody tests.

Relapse results from periodic release of infective merozoites from the liver. When the erythrocytic cellular and humoral protection against the erythrocytic phase of the disease is deficient or reduced by concurrent infection, age, trauma, or other debilitating factors, relapse of clinical malaria occurs until the erythrocytic cycle is again controlled by a humoral and thymus-dependent cell-mediated host response. True relapse, as opposed to a delayed exoerythrocytic cycle or a recrudescence of erthrocytic infection, generally will occur for up to 5 years with *P.vivax* and possibly 2-3 years for *P.ovale*. *P.malariae* appears to recur only as a recrudescent erythrocytic infection, sometimes lasting 30 or more years after the primary infection. *P.falciparum* may have a short-term recrudescence and also does not develop a true relapse from liver-developed merozoites because only one exoerythrocytic liver phase develops during *P.falciparum* infection.

Information concerning immunological resistance to malarial infection has been developed from a variety of sources over the years. See, e.g., Chapter 41 in "Basic & Clinical Immunology", 3rd Ed., Fudenberg, et al., eds. [Lange Medical Publications, Los Altos, Calif., (1980)]. Much of this information is based on African populations wherein the disease state is endemic. It has been determined, for example, that a very gradual long-term resistance to falciparum malaria is acquired in African populations. The resistance develops years after the onset of severe disease among nearly all children over 3 months of age. (Initial passive protection is present owing to transplacental maternal IgG.) There are estimates of a million malaria deaths a year in Africa, chiefly among children under five. Even after surviving childhood infection, a large proportion of adults nonetheless remain susceptible to infection and show periodic parasitemia, even though their serum contains "protective" antiplasmodial antibodies. In hyperendemic areas of Africa, it is believed that nearly all residents harbor a continuous series of falciparum infections of low to moderate pathogenicity throughout their lives. The immune response that leads to protection is thought to be the production of complement-independent antibody that inhibits entry of merozoites into the host erythrocytes. All immunoglobulin classes are elevated in the serum of malaria patients, but IgG levels appear to correlate best with the degree of malaria protection (or control of acute manifestations).

Chemical (drug) treatment of clinical symptoms rather than immunization has been the major focus of malaria research for decades. A first major approach to development of anti-malarial vaccines has involved attempts to induce protective immunity using sporozoites inactivated by, e.g., ultraviolet light, formalin or mechanical disruption. These agents reputedly induce a short-term, thymus-dependent, species- and strain-specific immunity active only against the exoerythrocytic, sporozoite infection. This approach has generally involved use of sporozoites dissected from irradiated mosquitoes or by inoculation through the bite of irradiated mosquitoes. Only mature infective sporozoites have been found to be immunogenic and adjuvants appear to be unnecessary. This method is limited by the difficulty in storing the vaccine; by inability to culture and therefore obtain large amounts of immunizing antigen; by the requirement of intravenous administration of the vaccine; and by the continuing susceptibility of the immunized person to a merozoite infection (should even a single sporozoite succeed in developing in the liver).

Recent attempts have been made to bring genetic engineering manipulative techniques to bear on development of specific proteinaceous isolates which might possess the protective antigenic capability of the entire sporozoite fragments. Success in these endeavors may result in alleviation of the generation, storage and delivery problems noted above. It will remain the case, however, that if a single sporozoite (from among hundreds injected by a single mosquito bite) survives the host's vaccine-induced immune response, a severe erythrocytic stage infection can ensue. See, Marshall, *Science*, 219, pp. 466-467 (1983).

A second general approach to immunization has involved use of killed or inactivated merozoite vaccines. See, generally, Cohen, *Proc.Royal.Soc.London*, 203, pp. 323-345 (1979). Research efforts in this area have been aided greatly by the procedures developed by Trager and Jensen [*Science*, 193, pp. 673-675 (1976)] relating to continuous culture methods for in vitro propagation of erythrocytic stages of parasites.

Merozoite vaccines are believed to induce formation of multiple antibodies, some of which react with red cell surfaces and selectively agglutinate infected cells, generally producing a strain- and species-specific alleviation of clinical symptoms. New infections can still develop, since there is no protection against sporozoites or the exoerythrocytic cycle. So long as the humoral antibody titer is high, however, merozoites (but not gametocytes) will be destroyed, and symptoms will generally not develop. Rhesus monkeys vaccinated with *P.knowlesi* merozoites (normally quickly killed by this form of malaria) have been reported to be fully protected for 18 months.

Freund's Complete Adjuvant (FCA) or synthetic adjuvants are required for merozoite antigen use and thus constitutes a major deterrent to development of a human vaccine. More recent studies using karyotype-selected *Aotus* monkeys infected with human *P.falciparum*, reported prolongation of life in owl monkeys vaccinated with parasite material cultivated in vitro when the synthetic adjuvant muramyl dipeptide was used instead of FCA. In the rhesus monkey immunization studies, helper T cells, other cell-mediated effector mechanisms, and humoral antibody all appear to be involved. Extracellular merozoites are specifically inhibited by IgG and IgM in the absence of complement. Immunization in Rhesus monkeys reportedly induces complete elimination of parasites after 1-3 weeks, whereas natural immunity following repeated infection and drug cure is associated with chronic relapsing parasitemia. Immunization probably is associated with far fewer soluble circulating antigens than natural infection, which preferentially stimulates suppressor cells or lymphocyte mitogens, all of which favor parasite survival. Among the difficulties associated with immunization with merozoites are risks of contamination of the merozoite vaccine with blood group substances acquired during its cultivation (inducing anemia) and substantial potential problems of vaccine delivery, cost, and acceptance.

Among the most recent reports of work relating to merozoite vaccines is that of McColm, et al., *Parasite Immunology*, 4, pp. 337-345 (1982). This publication followed the extensive prior report of Mitchell, et al., *Bull. W.H.O.*, 57, (Supp. 1), pp. 189-197 (1979) and of Desowitz, *Experimental Parasitology*, 38, pp. 6-13 (1975) in the ongoing study of the effects of various adjuvants on merozoite vaccine efficacy.

Apart from work directed to development of whole, killed or inactivated, merozoite vaccines, investigations spanning the last four decades have had as their focus the immunological properties of host and parasite antigens associated with the entirety of the erythrocytic stage of malarial parasite development. For example, antigenic proteins of parasite origin were detected in the plasma or serum of monkeys, ducks. rodents, chickens, and man with acute malaria as early as 1939. Partial protection against challenge infection was demonstrated in chickens and monkeys with blood plasma derived antigens of *Plasmodium gallinaceum* and *Plasmodium knowlesi*, respectively [Todorovic, et al., *Ann.Trop.Med.Parasitol.*, 61, pp. 117-124 (1967); Collins, et al., *Am.J.Trop.Med. & Hyg.*, pp. 373-376 (1977)]. Todorovic and his associates [*Am.J.Trop.Med. & Hyg.*, 17, pp. 685-694 (1968); *Am.J.Trop.Med. & Hyg.*, 17, pp. 695-701 (1968); and *Trans.R.Soc.Trop.Med.Hyg.*, 61, pp. 51-57 (1968)], demonstrated that fluorescein-conjugated antibody specific for soluble *P.gallinaceum* serum antigens reacted with free merozoites and was capable of activating macrophages. The antigens were labile to temperatures greater than 65° C., sensitive to proteolytic enzymes and contained a lipid component. Additionally, fluorescein-conjugated antibody prepared to the soluble antigens reacted with both infected erythrocyte cytoplasm and the parasite if the erythrocytes contained mature parasite forms. However, in erythrocytes containing immature ring forms, only the parasite was stained. Subsequent studies by these workers suggested that temperature, enzymatic degradation and antigen-antibody complexes occurring in the plasma of affected animals were among the elements which degraded the immunogenicity of these antigens and minimized their usefulness as vaccines.

McGregor, et al., [*Lancet*, 1, pp. 881-884 (1968)]; Wilson, et al., [*Lancet*, 2, pp. 201-205 (1969)]; McGregor, et al., [*Trans.R.Soc.Trop.Med.Hyg.*, 65, pp. 136-151 (1971)]; and Williams, et al., [*Af.J.Med.Sci.*, 4, pp. 295-307 (1972)], relate to demonstrations of the presence of soluble antigens in the plasma of human beings infected with an African strain of *P.falciparum*. Characterization of the majority of the soluble antigens found in the serum showed them to be heat stable at 100° C. [Wilson, et al., *Immunology*, 3, pp 385-398 (1973)]. Consequently, they were called "S" antigens. Molecular weights reported for S antigens ranged from 60,000 to 210,000 daltons. Groups of soluble plasmodial antigens not usually found in the serum ("La", "Lb", and "R" antigens), had properties different from S antigens. L antigens were reportedly more immunogenic than S antigens and rapidly reacted with antibody leading to soluble antigen-antibody complexes in the serum [Wilson, et al., *Lancet*, 2, pp. 201-205 (1969); Houba, et al., *Af.J.Med.Sci.*, 4, pp. 309-317 (1972); and Wilson, et al., *Immunology*, 3, pp. 385-398 (1973)]. Saul, et al., [*Tropenmed. Parasitol.*, 28, 302-318 (1977)] demonstrated that a soluble protein-containing immunogen could be obtained by washing sonically freed *P.berghei* parasites with cold saline. Further work by Kreier's group [Grothaus, et al., *Infect. and Immunol.*, 1, pp. 245-253 (1980)], is reported to show that the soluble material was more immunogenic than the intact parasites.

The occurrence of *Plasmodium*-associated antigens in infected plasma suggested that such antigens may be released from the parasitized erythrocytes. Membranes of erythrocytes parasitized with *P.knowlesi* that were thus subjected to immunochemical analysis have been shown to contain several proteins of parasite origin in the molecular weight range of 50,000 to 65,000 daltons [Wallach, et al., *J.Mol.Med.*, 2, pp. 119-136, (1977); and Deans, et al., *Parasitology*, 77, pp. 333-344 (1978).

The most recently reported developments in the proposed use of antigenic fragments associated with erythrocytic stages of malarial parasite growth have had their origins at the Wellcome Foundation in the United Kingdom. More specifically, U.K. published Patent Application Ser. Nos. 2,096,893 and 2,099,300 both report that, prior to the development described, "Attempts have been made to define the diversity of protein antigens associated with merozoites. However, no specific antigens capable of inducing a protective response by the host or specifically recognized by such a protective response have been isolated and characterized." Both published applications are said to relate to "protection inducing antigens of parasites of the genus *Plasmodium*" and both describe the use of affinity separations (involving monoclonal antibodies) to isolate merozoite and schizont form antigens.

As specific examples of practice of the development, both published British applications describe isolation of antigens associated with murine-specific malarial species, *Plasmodium yoelii*. Briefly summarized, erythrocytes from infected cells of mice are lysed, centrifuged and solubilized with a variety of detergents to yield a supernatant containing erythrocyte soluble proteins, some erythrocyte membrane proteins and an estimated "70% of the parasite antigens". The solubilized material is then passed through an immunoabsorbant column to which specific monoclonal antibodies were bound. The eluate of the antigen/antibody absorption is concentrated and dialyzed to yield non-glycosylated antigens having a molecular weight of $2.35 \times 10^5$ or $1.95 \times 10^5$ (assertedly corresponding to merozoite- and schizont-associated antigens). The antigenic isolates are reported to have been successfully used with Freund's Complete Adjuvant to protect mice against lethal challenge *P.yoelii* parasites. The applications go on to discuss similar attempts to isolate one or more antigens or antigenic fragments from *Plasmodium falciparum* parasitized erythrocytes, using a correspondingly specific monoclonal antibody. The resulting antigens were tested in vitro for cross-reactivity with *P.yoelii* antigen but not employed in any in vivo (antibody generation or infectious challenge) work.

Assuming that the projected isolations of *P.falciparum* schizont and merozoite antigens according to the procedures of U.K. published Patent Application Nos. 2,096,893 and 2,099,300 are as fruitful as the work reported for *P.yoelli* antigens, it is possible that the *solubilized* protein isolates may provide useful components for a human vaccine composition. Large scale production of antigenic materials, however, is likely to involve numerous difficulties, including problems in securing large quantities of human blood cells infected with late stages of parasites in large scale solubilization processing of erythrocytes free of red blood cell components, and in large scale maintenance and operation of antibody columns for affinity purification.

As previously noted, development of methods for continuous in vitro propagation of malarial parasites by Trager and Jensen, supra, has markedly assisted in the development of merozoite vaccines and the general study of erythrocytic malarial parasite stages. In a sense, it has also provided a means for detection and isolation of soluble antigens unaffected by the host's metabolic and immune systems. As an example of this type of research, most investigators found maximal quantities of protein material to accumulate in the culture medium during late schizogony and merozoite reinvasion. The possibility of the presence of Plasmodium-associated material in culture supernatant had been reported in cultures of *P.knowlesi* (Cohen, et al., 1969), *P.falciparum* (Wilson, 1974; Wilson and Bartholomew, 1975), and *P.berghei*, (Weissberger, et al., 1979). Wilson and Bartholomew (1975) detected antigens that were heat stable, partially heat labile and heat resistant, termed S, L and R antigens, respectively. Jepson, et al., *Acta.Path.Microbiol.Scand.*, Sect. C, 89, 99103 (1981) reported the isolation of two distinct antigens of the S and R classes from the culture medium of growth of *P.falciparum* in human erythrocytes. The isolation procedure involved immunoabsorbant techniques and is said to have yielded approximately 3 milligrams of the two antigens from 800 milliliters of culture medium. The results were said to "show promise for further attempts to isolate other antigens from the culture medium, and for obtaining knowledge about the chemistry and biology of the isolated antigens". Similarly, Thelu, et al., *WHO Bulletin*, 60, pp. 761–766 (1982) reports on the chromatographic isolation of an "Antigen E" from cultured *P.falciparum* and correlations between this substance and antigens in sera of human patients in endemic areas.

Of interest to the background of the invention is research generally involving use of immunological adjuvants and especially pertinent are those publications which discuss adjuvants believed to be suited for incorporation into malaria vaccines. Sometimes referred to as "immunopotentiators", adjuvants are ordinarily defined as substances which operate to increase the rate at which an immune response develops, or increase the intensity of the response, or prolong the response, or simply to allow for the development of any response at all to an otherwise essentially non-immunogenic substance. Adjuvants are commonly categorized as either general potentiators of both cellular and immune responses or specific potentiators of responses to only certain antigens. See generally, Chapter 24 of "Basic & Clinical Immunology", supra.

It has consistently been the case of the nonsporozoite materials displaying potential as anti-malaria vaccine components are so weakly immunogenic as to absolutely require the use of oil and water adjuvants such as Freund's Complete Adjuvant (FCA) to develop any effect. Such adjuvants are not accepted for use in humans. In anticipation of the discovery of truly protective anti-malarial antigens, substantial and relatively continuous efforts have been made in the screening of existing adjuvants and the development of new adjuvants for vaccine use. U.S. Pat. No. 3.849,551, for example, proposes the use of *Mycobacteria bovis*, strain Calmette-Guerin bacillus (BCG) as an adjuvant for malaria vaccines, and Schenkel, et al. [*J.Parasitol.*, 61, pp. 549–550 (1975)] propose mixtures of BCG with Adjuvant 65 as providing even more beneficial results. Desowitz [*Experimental Parasitology*, 38, pp. 6–13 (1975)] provided a comprehensive screening study of various adjuvants used with a *P.berghei*, blood-derived soluble antigens. Among the many results of tne study was the conclusion that ferric alum and aluminum chloride precipitated antigens were non-immunogenic while aluminum-alum-precipitated antigens might be protective. As previously noted, Mitchell, et al., supra, studied adjuvant effects for merozoite antigens and concluded that muramyldipeptide in mineral oil was partially effective in some studies and saponin was demonstrably effective in others. Siddiqui, et al. [*Nature*, 289, pp. 64–66 (1981)] reports on "effective immunization of monkeys with killed parasites and N,N-dioctadecyl-N',N'-bis(2-hydroxyethyl-propanediamine) McColm, et al., supra, reported the testing of numerous adjuvants with a killed parasite vaccine and concluded that none were as effective as saponin, although FCA, aluminum hydroxide and *C.parvum* augmented immunity considerably. Correspondingly, the aforementioned U.K. published Patent Application Nos. 2,096,893 and 2,099,300 report use of FCA in vaccination tests designed to illustrate potential utility for the isolated antigen, but note that "convenient" adjuvants for use in vaccines include saponin, *C.parvum* and aluminum hydroxide.

The above remarks with respect to the background of the present invention establish that, despite decades of costly investigation and determined effort by countless investigators, there continues to exist a need in the art for readily available materials demonstrably useful as protective immunogens in antimalarial vaccines.

BRIEF SUMMARY

The present invention provides, for the first time, anti-malarial vaccine compositions of demonstrable in vivo efficacy which are formulated through use of one or more proteinaceous immunogens readily isolatable from (1) the host erythrocyte-free and parasite-free supernatant fluid medium of in vitro cultured growth and proliferation of *Plasmodium* parasites in susceptible erythrocytes, and/or (2) washes, including hypotonic washes, of erythrocytes from parasite-infected cultures.

A presently preferred embodiment of the invention comprises vaccine compositions suitable for use in developing in human vaccinates a protective immune response against morbidity and mortality of *Plasmodium falciparum* infected. The preferred vaccine includes an immunologically effective amount of one or more proteinaceous immunogens characterized by molecular weights in the range of about 35,000 to about 85,000 daltons and further characterized by their isolation from the medium of in vitro propagated *P.falciparum* in mammalian erythrocytes, preferably human erythrocytes, and/or isolation from washes, including hypotonic washes, of erythrocytes used in *P.falciparum* cultivation. Principal immunogen isolates of the invention include two antigens having respective molecular weights of 42,000 and 54,000 daltons. In the preferred vaccine compositions are suitable carrier substances (e.g., balanced salt solution, PBS or culture medium) and suitable immunologically acceptable adjuvants, e.g., saponin, aluminum hydroxide and the like.

According to another aspect of the present invention, anti-malarial vaccine compositions exceptionally well-suited for human use are provided including the above-noted cell-free, culture medium-derived immunogen(s) in combination with an aluminum hydroxide adjuvant. In this regard, applicants have discovered such an adjuvant not only remarkably increases the immunological response of vaccinates to the proteinaceous antigen, but also increases both the rate and duration of response as well. A presently preferred form of aluminum hydroxide for use in vaccine compositions is Alhydrogel (Superfos).

In another of its aspects, the present invention provides a series of procedures for the optimization of the in vitro growth of *P.falciparum* parasites in long-term human erythrocyte cultures leading to the large scale production of human erythrocytes infected with late stage parasites and optimal production of culture medium supernatant and wash-derived immunogens. Briefly, cultures are initiated and sub-cultures are developed through use of cells and serum pre-screened for matching histocompatibility factors (e.g., major blood groups) and incompatibility of serum to erythrocytes in the context of "warm" and "cold" antibody/antigen reactions.

Further aspects and advantages of the present invention will become apparent upon consideration of the following detailed description of presently preferred embodiments thereof.

DETAILED DESCRIPTION

The following illustrative examples of practice of the present invention are directed to presently preferred procedures for obtaining the active proteinaceous immunogens employed according to the invention, for formulating vaccine compositions through use of the antigens with selected adjuvants and for using vaccines so formulated to develop protective immunity in susceptible vertebrates against infection by plasmodial parasites.

More specifically, Examples I and II are directed to procedures for in vitro cultivation of *P.falciparum* parasites in human and non-human erythrocyte cultures. Example III is directed to procedures for isolating antigens from tne fluid culture medium of parasite propagation and from washes of infected erythrocytes. Example IV is directed to characterization of physical and in vitro immunological properties of antigens so obtained. Example V describes the preparation of specific vaccine compositions according to the invention which employ the culture-derived antigen along with exemplary saponin and aluminum hydroxide adjuvants.

Example VI relates to vaccination and challenge studies performed on squirrel monkeys using vaccine compositions of the invention. This example demonstrates immune responses of the test animals to vaccine compositions including a saponin adjuvant, in terms of both pre- and post-challenge humoral responses and in terms of clinical manifestations of the challenge infection.

Example VII relates to the post-vaccination humoral responses of an animal treated with vaccine compositions including an aluminum hydroxide adjuvant. Example VIII relates to vaccination and challenge studies performed on squirrel monkeys using vaccine compositions of the invention with an aluminum hydroxide adjuvant. Example IX relates to in vitro growth inhibition studies employing immune serum of vaccinated animals.

EXAMPLE I

This example relates to procedures for in vitro cultivation of *Plasmodium falciparum* in erythrocytes derived from squirrel monkeys (Saimiri sciureus). An Indochina I strain isolate of *P.falciparum* was obtained from Dr. C. C. Campbell of the Center for Disease Control, Atlanta, Ga. This organism had been isolated from infected human cells, had been adapted for growth in, and is pathogenic for, squirrel monkeys and remains pathogenic for humans.

A. Preparation and Reactivation of Stabilates

An initial series of procedures involved in the in vitro cultivation of *P.falciparum* in mammalian erythrocytes relates to the preparation of a frozen stored "stabilate" of infected cells (from animal and culture sources) and the reactivation of such a stabilate for use in the initiation of cultures.

Preparation of a stabilate from an animal source or from infected cells in culture may be effected by mixing either whole infected heparinized blood or washed, infected erythrocytes from cultures in a 1 to 1 volume ratio with 20% glycerol in a balanced salt solution comprising (per liter): distilled water (1 liter); dextrose (1 gram); $KH_2PO_4$ (60 mg); $Na_2HPO_4.7H_2O$ (358 mg); phenol red (10 mg); KCl (400 mg); NaCl (8 g); $MgCl_2.6H_2O$ (200 mg); $MgSO_4.7H_2O$ (200 mg); and $CaCl_2.2H_2O$ (186 mg). Alternatively, washed infected erythrocytes from culture may be admixed in equal volumes with a cryopreservative solution made by adding 70 ml of glycerol to 180 ml of a 4.2% solution of sorbitol in 0.9% sodium chloride which has been sterilized by filtration. After the mixing procedure, cells are immediately transferred to Nunc vials for storage in liquid nitrogen.

Reactivation is accomplished upon removal from liquid nitrogen by thawing at 37° C. without agitation until a slurry of cells is formed without appreciable lysis of cells. Erythrocytes are settled by gentle centrifugation (about 500×g), the supernatant is discarded, and each volume of cells is brought up gently in an equal volume of 3.5% sodium chloride wash solution and allowed to stand at room temperature for five minutes.

The cells are again centrifuged gently, the supernatant is discarded, and the packed cells are then brought up in two volumes of complete medium including serum (as described below). Following centrifugation the packed cells are then ready for admixture with uninfected erytnrocytes.

B. Screening of Cells and Serum

Another initial series of procedures involved in in vitro cultivation of P.falciparum in mammalian erythrocytes relates to pre-screening cells and serum to be employed in the cultures so that in vitro propagation of parasites may be optimized. A first measured parameter of candidate erythrocytes is their osmotic stability. Briefly, approximately 5 ml of each potential uninfected cell source is washed three times in serum-free culture medium. If any cell lysis occurs during any wash, the cells are ciscarded as too fragile for culture purposes.

All candidate sera and plasma are screened for major blood group histocompatibility with both infected and uninfected cells to be employed in cultures by simple admixture in microtiter plates at room temperature and microscopic monitoring for agglutination. Typically, adverse effects use of serum sources containing, e.g., anti-A antibodies with A cells will be avoided by these procedures. Room temperature screening for agglutination also serves to eliminate serum sources possessing so-called "cold antibodies" (to M and P erythrocyte antigens). If no clotting or agglutination occurs, plates are covered, placed in a humidified incubator at 37° C. and monitored for agglutination at 1 hour, 3 hours, and overnight to detect agglutination which may be due to "warm antibodies", e.g., anti-$Fy^a$-$Fy^b$, anti-$JK^a$, and anti-K. It has been determined that screening for compatability in terms of Rh factors is not absolutely required for success of in vitro cultivation procedures according to the invention. Parasites appear to propagate well, for example, in A+ or A- cells, but show a preference for A- cells.

The totality of the above-noted screening procedures series to allow for the use in cultures of erythrocyteand serum or plasma combinations wherein erythrocyte antigens are non-reactive, over all culture thermal ranges, with saline reactive and atypical antibodies present in the serum or plasma.

A final screening of cells and serum prior to initiation of large scale cultures involves testing for susceptibility to parasite infection. A 10% suspension of parasitized erythrocytes is placed in each of three microliter plate wells with 180 μl of medium including serum and a similar suspension of uninfected red cells to generate an initiai parasitemia of from about 0.25 to 0.4%. The plate is incubated and Giesma-stained films are made daily over three days to monitor for minimal parasitemias of about 3 to 6%.

C. Parasite Cultivation in Monkey Cells

The method of parasite cultivation employed is a modification of the described by Trager and Jensen, supra, Parasites are cultured in 35 × 10 mm Falcon tissue culture dishes (1.5 ml of the 10% suspension/dish) anc incubated at 37° C. in candle jars or in Corning 25 $cm^2$ tissue culture flasks (5.0 ml/flask) under a precision gas mixture atmosphere of 6% $O_2$, 10% $CO_2$, and 84% $N_2$. The culture supernatant medium is replaced once or twice daily; medium containing 10% monkey serum is used to maintain cultures.

Blood from animals with 0.5% to 5% parasitized erythrocytes was used to initiate in vitro cultures of the organism. More specifically, a 5 to 10% suspension of washed infected monkey erythrocytes (initial percent infected erythrocytes 0.5 to 0.8%) in RPMI 1640, supplemented with sodium bicarbonate and HEPES (pH 7.0) and 15% normal monkey serum were used to initiate cultures.

Gentamicin (Gentocin, Schering Corp., Kenilworth, N.J.) in a concentration of 0.1 μl/ml to 1.0 μg/ml of complete medium was employed as an anti-microbial agent. Concentrations greater thjn 10 μg per ml were toxic to parasites.

Since activated macraphages destroyed parasitized erythrocytes in vitro, they were removed from white blood cells using Ficoll-Hypaque (Pharmacia Fine Chemicals, Piscataway, N.J.) prior to culturing parasitized monkey erythrocytes or subculturing with normal monkey erythrocytes.

Percentages of parasitized erythrocytes in culture were microscopically determined by staining blood films with Giemsa (Sigma Chemical Co., St. Louis, Mo.).

Several culture lines were initiated and terminated after varying growth periods ranging from 5 to 21 days. Daily microscop9c examination of P.falciparum cultures revealed multiplication of the organism. The beginning parasitemia of 0 5%-increased to an average of 4% within 72 hours of incubation. Subcultures were made when parasitemias were between 2% and 4% in order to provide for continuation of the line. On occasion, parasites were grown 5 or 6 days without subculture resulting in an average peak parasitemia of about 8.5%. An active multiplcation of the Organism was also detected by the appearance of all growth forms of Plasmodium, beginning with ring forms, through trophozoite, schizont and merozoite stages. While Minimum Essential Medium (Eagle 138 Special, Gibco Laboratories, Grand Island, N.Y.) also supported the growth of P.falciparum in squirrel monkey erythrocytes, there was no apparent advantage of using this medium over RPMI 1640. Medium 199 supplemented with penicillin-streptomycin did not support the growth of P.falciparum Indochina I in the primate culture system.

EXAMPLE II

The procedures of Example I, including the pre-screening procedures proved equally applicable for cultivation of P.falciparum in human erythrocyte/human serum systems. Thus far, four strains of P.falciparum have been cultured in human crythrocytes (A positive) and human serum or plasma reconstituted in $CaCl_2.2H_2O$. These strains are: Indochina I; Honduras; Geneve (Senegal) and Lili. A iftn line (Monkey-Human) arose from the successful transfer and adaptation of Indochina I parasitized erythrocytes from an infected Saimiri monkey to culture containing human erythrocytes and human sera. In sum, application of the above procedures allow for the cultivation of infected monkey erythrocytes in the presence of human cells and sera, and of infected human erythrocytes in the presence of pooled Saimiri sera in addirion to homologous culture systems.

For antigen production in a human system, several large vials of stabilate of the desired strain(s) of P.falciparum are reactivated inro 5 ml or 15 ml flasks using a precision gas mixture. Simultaneously, each strain of P.falciparum is cultured in duplicate 35 mm dishes using candle jar methods as a back-up system. Similarly, two dishes conraining uninfected erythrocytes are cultured. Within three days to one week subsequent to reactivation, infected erythrocytes are subcultured into six to ten flasks (150 cm$^2$) in addition to a continuous flow vessel using precision gas. Plasmodial strains are subcultured alternately every third followed by every fourth day (e.g., two times each week). Within three subcultures, 80 ml of parasitized erythrocyte suspension optimally generates 800 ml followed by 8,000 ml of culture supernatant using the flow vessel alone. Using the latter vessel, the work is accomplished with a minimum of labor. To allow for maximum peak parasitemia without loss of culture lines, parasites are subcultured to lower parasitemia levels of about 0.2% ar the beginning of the fourth day growth period, and alternately are subcultured down to about 0.4% prior to the third day growth period. Consequently, approximately the same peak parasitemia level is being maintained throughout the cultivation period.

The following specific cultural procedures and gas mixtures have been used in order to accomplish antigen production in human cell systems. Parasites grown in microtiter plates or in 35 mm dishes are placed in a candle jar in order to obtain the reduced oxygen tension necessary for the growth of Plasmodium. Parasites grown in 25 cm$^2$ flasks, 75 cm$^2$ flasks, 150 cm$^2$ flasks or flow vessels, are grown under a precision gas mixture of 6% oxygen, 10% $CO_2$, and 84% nitrogen. In the flow vessel, the incubator is not flooded with the precision gas mixture; the gas line is guided directly into the flow vessel. In the plates or in the flasks, culture suspensions are maintained in a stationary position. In contrast, in the flow vessel, following the mixing of infected and uninfected erythrocytes with media on subculture days, the flow vessel is rocked at a very slow speed for approximately twenty minutes prior to stopping it and bringing it into a stationary position. For optimal parasite growth the flow vessel should be rocked only twice daily for fifteen minutes each time, and not continuously, to allow for the proper mixing of nutrients.

EXAMPLE III

This example relates to procedures for isolation of soluble proteinaceous immunogens resulting from cultured growth and proliferation of P.falciparum as described in Examples I and II.

Three types of antigenic preparations are available from cultured growth of infected erythrocytes, depending on the manipulations performed on culture materials. These three preparations are referred to respectively as "supernatant", "wash", and "hypotonic wash" antigens.

"Supernatant antigen" is obtained from the daily collection of complete culture medium employed to support growth of organisms.

"Wash antigen" is generated at the time parasitized erythrocytes are subcultured. Following the removal of the supernatant culture medium an equal volume of incomplete (serum-free) medium is added to the infected erythrocytes. This suspension is then gently centrifuged to allow for pelleting of the erythrocytes. The supernatant constitutes the wash antigen. In the flow vessel, for example, 8 ml of packed infected erythrocytes are combined with 75 ml of incomplete medium and rocked for about one-half hour. At that time the rocker is stopped, erythrocytes are allowed to settle, and the supernatant which is removed constitutes the wash antigen.

"Hypotonic wash antigen" is produced by subjecting a washed infected erythrocyte suspension to a second washing as described above using incomplete culture medium in order to remove any contamination derived from complete serum-containing medium. The supernatant of the second washing is first removed and discarded. To the remaining infected erythrocytes 75 ml of a typical hypotonic solution composed of 60 ml of incomplete medium and 30 ml of sterile distilled water is then added. The suspension is rocked at 37° C. under the precision gas mixture for approximately one-half hour. The rocker is stopped, erythrocytes are allowed to settle, and, approximately 24 hours later, supernatant medium is collected. In the course of this procedure the particular hypotonic solution employed is one which allows the cells to swell without lysis (thereby avoiding the presence of large amounts of erythrocytic materials in the hypotonic wash and permitting cells to be readily used in subculturing procedures).

Supernatant, wash and hypotonic wash antigen preparations are centrifuged to remove any erythrocyte and parasite cells and cell debris and kept frozen at −70° C. Pools of the antigen preparations are made, sequentially filtered through 0.45$\mu$ and 0.22$\mu$ millipore filters (Sybron/Nalge, Rochester, N.Y.) and then concentrated 10- to 15-fold by pressure dialysis.

EXAMPLE IV

This example relates to characterization of properties of proteinaceous antigen preparations obtained according to Example III.

A. Ouchterlony Tests

A first characterization study of soluble, culture-derived P.falciparum antigens involved testing in the Ouchterlony (or double diffusion in two dimension) system frequently employed for qualitative identification of antigen-antibody systems. Various concentrations of mixed supernatant and wash antigen derived from human cultures (1.25×, 2.5×, 5×, 10×, 17× and 68×, all representing concentrations of normal culture supernatant and infected culture supernatant) were placed in wells surrounding a central well of antibody on an agar-coated plate. Antigen and antibody migrate toward each other in the medium and at the zone of equivalence they form a line of precipitation if a reaction occurs between the antigen and the antibody. The relative position of the precipitin line is determined by the concentration of the antigen relative to the concentrations of the antibody in the agar. The local concentration of each respective reaction is dependent on its absolute concentration in the well and also in its molecular size and rate of diffusion through the gel.

The Ouchterlony test was conducted by a modification of the method described by Hudson and Hay, 1976. Slides were coated with 1% Nobel agar in barbital buffer. As a modification, 4% polyethyleneglycol was added to the gel to concentrate the precipitin lines in positive reactions. After the agar hardens a template is used to punch out the wells and the agar plugs are removed by vacuum-suction. Wells are filled with the respective reagents. The plate is incubated at room temperature in a humidified chamber for 24 hours. If no precipitin lines are visible, plates are incubated for 24 hours at 4° C. This technique has the advantage of comparing many antigens or concentrations of a single antigen with a single antibody source. Thus, the degree of homology among antigens can be determined. The following types of reactions can be obtained: reactions of identity where the antigens would be identical to each other, non-identity where there are no shared epitopes or antigenic determinants, or partial identity where antigens are not identical but some antigenic determinants are shared.

Two test systems using double diffusion gel have afforded relevant information. The first was a control system which utilized normal human sera and normal Saimiri sera (both unconcentrated) as antigen and (2× concentrated) rabbit anti-monkey globulin, as well as (2× concentrated) rabbit anti-human globulin in the anti-sera wells.

This control test system resulted in a reaction of partial identity between human and monkey sera with respect to both anti-sera, indicating (1) shared antigens between human and monkey sera, and (2) antigens missing from the monkey material that were present in the human sera. This result supported the desirability for purification of the human-derived supernatant antigens employed in monkey vaccination studies in order to avoid anemia or interference with the anti-plasmoidal response.

The second test system employed crude supernatant antigen from the human system and IFA positive antisera from the Example VII monkey (vaccinated with supernatant antigen and an aluminum hydroxide adjuvant). Owing to the general lack of sensitivity of the procedure, antigen preparations were concentrated 68× to assist in visualization of the reactions. Detection of a positive precipitant line between the immune reactants indicated that the antibody raised to the soluble antigen vaccine specifically recognized Indochina strain *P.falciparum* soluble antigens in human culture supernatants.

B. SDS-Page Analysis

Samples of antigen preparations were analyzed by sodium dodecyl sulfate-polyacrylamide gel eletrophoreses (SDS-PAGE). Unconcentrated or concentrated culture supernatant antigen preparations from the culture of the Indochina I, Honduras and Monkey-Human strains of *P.falciparum* were obtained. The protein was precipitated with trichloroacetic acid, washed, dried and dissolved in 100 μl of phosphate buffer (0.01 M, pH 7.1), 1% SDS and 1% 2-mercaptoethanol. The samples were boiled at 100° C. for three minutes. Subsequently, they were chilled and 5 μl each of 1.01% of bromophenol blue and 2-mercaptoethanol were added. Following mixing, 5 μl of the above solution was added to each track on 7.5% or 10% polyacrylamide gels and electrophoresed.

Protein samples from the above-mentioned strain of *P.falciparum*, as well as normal culture supernatant were run against low molecular weight protein standards (Bio-Rad Laboratories, Richmond, Calif.) which included phosphorylase B (MW 100,000), bovine serum albumin (MW 68,000), ovalbumin (MW 43,000), carbonic anhydrase (MW 29,000), soybean trypsin inhibitor (MW 22,000) and lysozyme (MW 14,000). As set out in Table 1, below, following staining and calculations, a single band having a molecular weight range of about 49,000 daltons was reproducibly obtained from unconcentrated Indochina, Honduras, and Monkey/Human supernatants as well as from concentrated Indochina supernatants from human cell cultures.

A 10% SDS-PAGE examination of the Indochina (human cell) culture supernatant that had been concentrated eight times revealed two bands in place of the above single band of 49,000. These two bands had molecular weights of 54,000 and 46,000 daltons. Based on the possibility that soluble antigens may be only partially precipitated by TCA, modification and optimization of the SDS-PAGE system was undertaken.

Culture supernatants were concentrated by pressure dialysis using the Amicon diaflo system. Concentrated culture supernatants were lyophilized, reconstituted in distilled water, concentrated 2× and dialyzed with phosphate buffer containing SDS. One hundred ml of the 2× concentrated supernatant was incubated for three hours at 37° C. Samples were brought to room temperature. Five ml of 2-mercaptoethanol and 5 ml of 0.25% bromophenol blue were added to the 100 ml of the protein mixture. Seven ml was loaded onto the track and pre-electrophoresed for one-half hour at 150 milliamps. Following preelectrophoresis, samples were electrophoresed at 190 miliamps for 4½ hours prior to staining. In optimization of the system, it was found that in order to pick up the antigens, it is better to run the samples for three hours at 37° C. than to boil for three minutes at 100° C. Also, in examining concentrations of supernatants ranging from unconcentrated supernatant to supernatant that was concentrated 34 times, it was found that the optimal concentration of the supernatant for detection of these antigens is 2×.

Use of the above system reproducibly detected two bands in the Indochina infected supernatant of human erythrocyte cultures but not in negative (non-infected) samples. The molecular weights of the two bands obtained in three sets of consecutive tests are as follows: 40,738 and 51,286; 40,738 and 56,234; 45,709 and 53,703. The calculated average molecular weight of the two bands was: 42,395 and 53,741.

An examination of supernatants used in the two vaccination experiments (infra) and their respective controls on SDS-PAGE gels revealed that the number of protein bands and their positions in supernatants containing Saimiri serum is not identical to those supernatants containing human serum. The same observation was made on corresponding control samples. However, some bands were common in their position and intensity. As expected, an analysis of Indochina (human cell) supernatants revealed the previously described two bands (MW 37,153; 51,286). At least two bands were present in supernatant material derived from primate cultures used in the second vaccination experiment that were not found in the proper normal controls.

Formalin-treated supernatants derived from primate cultures, as well as formalin-treated supernatants derived from Indochina (human cell) cultures that were used in the vaccination procedures (infra) were also examined on gels with SDS. The pattern was almost identical between the material from the human system and the primate system with respect to: (1) protein bands missing (apparently destroyed); and (2) bands still present. It does appear that treatment with formalin resulted in the loss of ability to define both protein bands that can be found in non-formalin-treated infected supernatants. With slight modification of the treatment method, formalin appears to be a useful component for formulation of vaccines intended for human use.

TABLE 1

| Material | Molecular Weights (daltons) on SDS-PAGE | |
|---|---|---|
| | 7.5% Gel | 10% Gel |
| Indochina concentrated | 83,000 and 46,000 | |
| Honduras unconcentrated | 49,000 | |
| Indochina unconcentrated | 49,000 | |
| Monkey/Human unconcentrated | 49,000 | |
| Indochina (human cell) concentrated | | 54,000 and 42,000 |

C. PAGE Analysis

Samples of antigen preparations were also analyzed employing polyacrylamide gel electrophoresis (PAGE) without use of SDS. This procedure allows proteins to remain in their native configurations.

Concentrated supernatant preparations are lyophilized and diluted in distilled water to 2× concentration. This material is then dialyzed against TRIS-Glycine sample buffer. To 100 μl of sample buffer, 5 μl of 0.25% bromphenol is added. Following pre-electrophoresis at 50 milliamps for ½ hour, 7 μl of the sample is loaded onto the track. Concentration of the sample requires 10 minutes at 20 milliamps; samples are then electrophoresed at 40 miliamps for 4½ hours. Following electrophoresis, protein bands are stained with Coomassie blue.

Analysis of PAGE gels without SDS revealed two bands in infected culture supernatant, which are not present in uninfected cell supernatants. The first band was a very distinct, concentrated line that was located closer to the track and just below heavy staining (normal human serum) marker band. The second band was further away from the track and above the marker band; it is broader and has a lower band below it that is common to a faintly seen band occurring in norma culture supernatant.

Wash antigen and hypotonic wash antigen preparations were also analyzed by PAGE procedures. A comparison of wash to supernatant antigen preparations expectedly revealed fewer proteins in the wash antigen and the absence of the above-noted first, lower band close to the track. The hypotonic wash antigen, on the other hand, revealed this band but the second, upper band was missing. Because PAGE does not provide accurate molecular weight information, no correlations to the two characteristic antigens (of differing molecular weights) revealed by SDS-PAGE could be made.

Soluble supernatant antigens were analyzed by ion exchange chromatography using DEAE Sephadex A-50 (Pharmacia Fine Chemicals). The buffer used in the column was Tris-HCl pH 7.6. Indochina I supernatant derived from human cultures and concentrated ten times was employed for fractionation by this method. Conventional protein peaks representing gamma globulins and albumin were first revealed. A discernible protein peak was detected in tubes proximal to the albumin peak. The protein present in this peak was identified to be of malarial origin by means of the ELISA system. This activity was not detected in the supernatant obtained from non-parasitized cultures. The SDS-PAGE techniques verify the identity of this fraction with that obtained from the supernatant.

Figure 7A:
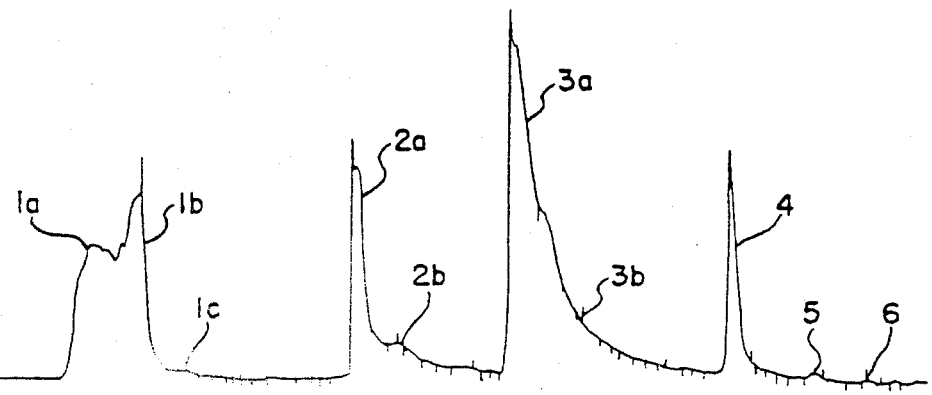
Figure 7B:
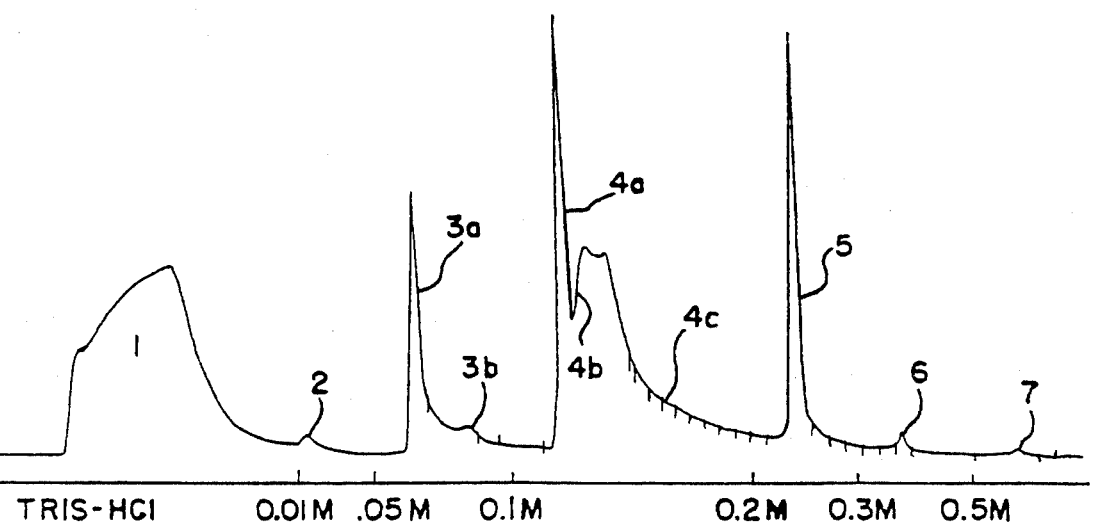

Another chromatographic system employed DEAE (diethylaminoethyl) Cellulose 52 (Whatman) as an anion exchanger. Infected culture supernatant of Indochina strain in human cells was fractionated and normal culture supernatant prepared under identical conditions served as a control. In both cases 60 ml of the unconcentrated culture supernatant was applied to the column with fractions being eluted using 0.01 M, 0.05 M, 0.1 M, 0.2 M, 0.3 M, and 0.5 M NaCl in TRIS-HCl starting buffer. Fraction pools were prepared after reading optical densities at 280 nm. As applied to infected and uninfected cell culture supernatants the fractionation system revealed a number of elution product peaks which appeared to be unique to the infected cell supernatant. (Compare FIGS. 7A and 7B).

As a preliminary test of immunogenicity in a mouse model, vaccination studies were conducted to ascertain whether any peak or either of the unfractionated culture supernatants was capable of provoking generation of antibodies detectable in an IFA screen. Uninfected and infected unfractionated supernatants were employed to vaccinate groups of four Balb C mice; individual fractions were collected and each employed to vaccinate groups of three mice. Dosages consisted of 0.25 ml of 10× concentrations of the appropriate individual fraction or unfractionated material, combined with 0.05 ml of aluminum hydroxide adjuvant as prepared in Example 5, infra. Primary and secondary vaccinal doses were given 21 days apart and blood was drawn and tested for IFA titers eight and twenty days after the primary vaccinal dose and twelve days after the secondary vaccinal dose. Tables 2 and 3 below, set out the results of the procedure, indicating that five fractions present in the infected cell supernatant and the unfractionated material consistently stimulated a positive antibody response ("Pos"). No discernible antibody response ("Neg") was elicited in the mice by the unfractioned uninfected culture supernatant or by any fraction thereof.

TABLE 2

| | Normal Culture Supernatant | | |
|---|---|---|---|
| Fraction No. (See FIG. 6A) | Protein Conc. μg/ml | Elution Molarity | Immunogenicity |
| 1a | 647 | Tris-HCl* | Neg. |
| 1b | 2135 | Tris-HCl | Neg. |
| 1c | 382 | Tris-HCl | Neg. |
| 2a | 2122 | 0.05 M** | Neg. |
| 2b | 3022 | 0.05 M | Neg. |
| 3a | 3202 | 0.10 M | Neg. |
| 3b | 487 | 0.10 M | Neg. |
| 4 | 885 | 0.20 M | Neg. |
| 5 | 162 | 0.30 M | Neg. |
| 6 | 172 | 0.50 M | Neg. |
| Unfractionated | 4700 | — | Neg. |

*Starting Buffer
**NaCl

TABLE 3

| | Infected Culture Supernatant | | |
|---|---|---|---|
| Fraction No. (See FIG. 6B) | Protein Conc. μg/ml | Elution Molarity | Immunogenicity |
| 1 | 777 | Tris-HCl | Neg. |
| 2 | 182 | 0.01 M | Pos. |
| 3a | 235 | 0.05 M | Neg. |
| 3b | 892 | 0.05 M | Pos. |
| 4a | 87 | 0.10 M | Neg. |
| 4b | 1772 | 0.10 M | Neg. |
| 4c | 477 | 0.10 M | Neg. |
| 5 | 622 | 0.20 M | Pos. |
| 6 | 200 | 0.30 M | Pos. |
| 7 | 177 | 0.50 M | Pos. |
| Unfractionated | 4950 | — | Pos. |

The five fractions, some relatively "pure" (i.e., free of normal serum and red cell components) were determined to have molecular weights in the range of 35,000 to 85,000 daltons. Specific active fraction molecular weights of infected cell supernatant were as follows: Fraction 2, 83,176, 72,444 and 56,234; Fraction 3b, 85,114, 67,608, 52,481, and 47,863; Fraction 5, 51,286; Fraction 6, 79,433, 45,709 and 31,623; and Fraction 7, 79,433.

D. Temperature and Enzyme Sensitivity

Temperature sensitivity and enzyme sensitivity screens were run on supernatant antigen preparations with results determined by PAGE. Heat treatment of culture supernatants at 37° C. and 56° C. for one-half hour did not alter the presence, position or intensity of the two distinct PAGE protein bands characteristic of supernatants of infected cells, while treatment at 100° C. for 5 minutes destroyed the ability to detect these bands upon staining. Enzyme treatments involved use of two different non-specific proteases, alpha amylases from two different sources, pancreatic lipase from two different sources, papain and a mixed glycosidase which attacks CHO bonds generally. Enzyme reagents were prepared at concentrations of 0.1 mg/ml of pH 7.2 phosphate buffered saline (PBS). 0.01 ml of each enzyme reagent was added to 100 μl of 2× concentrated [Indochina (human cell)] supernatant from infected and uninfected control cultures and enzymatic reactions were allowed to proceed at 37° C. for 16 hours, whereupon PAGE analysis was conducted as above. Both non-specific proteases destroyed all protein bands on PAGE; neither of the lipases nor the mixed glycosidase, nor did the papain have any effect on the two characteristic antigen bands. The first amylase appeared to lighten the intensity of the band farthest from the track, while the second amylase appeared to result in a broadening of the top band.

Preliminary supporting evidence for the glycoprotein status for at least one soluble proteinaceous antigen of the invention is a positive Periodic Acid Schiff (PAS) staining of a specific band found in the positive (and not negative) supernatant.

EXAMPLE V

This example relates to preparation of vaccine compositions according to the invention.

Vaccines employing proteinaceous immunogen concentrates obtained according to Example III are formulated with Saponin (1:15 volume in PBS) (Quil-A, Superfos Export Co., Vedback, Sweden) by simple mixture of equal volumes of antigen and adjuvant.

Vaccines employing the antigen concentrates and an aluminum hydroxide adjuvant are formulated through use of an adjuvant water solution containing 2.0 mg Al(OH)$_3$ [Alhydrogel, Superfos Export Corp.] and 6.9 mg merthiolate (or a similar dose of other preservative) per ml. This adjuvant solution is mixed with antigen concentrates in varying proportions.

EXAMPLE VI

This example relates to vaccination studies on squirrel monkeys wherein all animals were vaccinated with the saponin adjuvant/concentrated mixed supernatant and wash antigen compositions from monkey cell cultures of Example 1.

A. Animals

Male squirrel monkeys of Bolivian origin were purchased from South American Primates, Inc., of Miama, Florida. Animals were housed individually in stainless steel cages and maintained on a diet of high protein monkey chow (Ralston Purina Company) and tap water ad libitum. Monkeys received three fruits daily and 20 μl of a vitamin supplement (Vi Sorbin, Norden/Smith Kline, Lincoln, Nebr.) twice weekly.

Animals were rested and acclimated for a minimum of three weeks prior to experimental use. During this time, animals were processed through all examinations as required by the public health authorities. These included testing for exposure to Mycobacterium. One tenth ml of tuberculin (Jensen Salsbury Laboratories, Kansas City, Mo.), was injected intradermally above the upper eyelid. The test was read at 24, 48, and 72 hours for the presence of positive delayed type hypersensitivity reaction. Animals were screened for the presence of blood parasites by microscopic examination of thick and thin Giemsa-stained blood films. The presence of intestinal parasites was ascertained by examination of fecal samples.

Blood serum was tested for the presence of anti-plasmodial antibodies by means of an Indirect Fluorescent Antibody (IFA) test which used *P.falciparum* (Indochina I)-infected Saimiri erythrocyte as antigen. Squirrel monkeys naturally infected with *P.brasilianum* or *P.simium* produce antibodies that cross-react with *P.falciparum* in the IFA test.

B. Analytical Procedures

1. Parasitemia Determinations

As was the case with cells in culture, percent parasitemia in animals was determined by microscopic analysis of Giemsa-stained blood films.

The number of parasites/mm$^3$ of blood in challenged animals was determined by enumerating free *P.falciparum* parasites on Giemsa-stained thick smears. A 5 μl sample of infected blood was obtained from the calf portion of the leg of infected animals by cleaning the shaved area with 95% ethanol, sticking with a sterile lancet and drawing blood to the 5 μl mark in a microsampling pipet (Corning, Arthur H. Thomas Co., Philadelphia, Pa.). Blood was quickly transferred to a glass slide and spread uniformly in an area of specific length and width. Unfixed, Giemsa-stained smears were examined and parasites enumerated with the aid of a Howard grid. Five sweeps were made across the width of each smear and the contents of the entire grid were counted. The number of parasites counted was converted into number of parasites/mm$^3$ of blood.

2. Indirect Fluorescent Antibody Tests

Whole blood was obtained from the femoral vein of a squirrel monkey having 2% or greater erythrocytes infected with *P.falciparum* (Indochina I strain). Panheparin or ACD were used as anti-coagulants. The blood was centrifuged, the plasma was removed, and red cells were washed twice in phosphate buffered saline. Packed red cells were reconstituted in 1.75% bovine albumin (Fraction V, Miles Laboratories, Inc.) in PBS (pH 7.2) in a ratio of 40% packed cells to 60% diluent. One drop of diluted infected red cells was placed on an unfrosted, 95% ethanol-cleaned 3″ by 1″ glass slide and the blood was pushed with a second slide to cover uniformly the entire length of the slide. Slides were rapidly air dried with the aid of a fan, individually wrapped in tissue paper and stored at −70° C. in plastic locking bags. The addition of a packet of silica powder to the bag prevents the accumulation of moisture.

When needed for the test, slides were rapidly transferred to a desiccator and were desiccated overnight. Twenty-four hours later slides were fixed in acetone for ten minutes and air dried. Depending upon the length of the smear 10 to 14 circles were drawn on each slide with Martex ink. Clot-extracted serum was obtained from the femoral or saphenous vein of uninfected, immunized or infected squirrel monkeys at appropriate intervals. Admixed in microtiter wells (Costar 96-well tissue culture clusters, flat bottom, Cambridge, Mass.) were 20 μl of serum and 180 μl of phosphate buffered saline (pH 7.2). Successive two-fold dilutions of the 1:10 serum dilution in the first well were prepared and a 20 μl sample of each well was examined by IFA as follows:

The first circle contained a 1:10 dilution of the negative control, normal Saimiri serum. The second circle contained a 1:10 dilution of the positive control, serum obtained from an animal infected (i.v.) with the Indochina I strain of *P.falciparum*. Positive and negative controls were run on every slide.

Slides containing serum dilutions were incubated at 37° C. in a humidified incubator for 30 minutes. Excess serum was tipped off of slides and slides were washed twice gently in PBS and once in distilled water using a mechanical rotator. When slides were completely dry, 20 μl of a 1:30 dilution in PBS of fluorescein-conjugated IgG fraction of goat anti-monkey serum (Cappel Laboratories) was added to each circle. It was necessary to centrifuge the fluorescein-conjugated serum (diluted) just prior to use to avoid nonspecific fluorescence. Slides were reincubated for 30 minutes at 37° C. in a humidified incubator, rewashed as stated above, dried and covered with a cover-glass using mounting medium. Each circle was examined for the presence of fluorescence and its location with reference to the cell and to the parasite.

3. In Vitro Growth Inhibition Tests

A significant biological in vitro assay was employed to determine the capacity of sera from immunized monkeys to inhibit growth and development of *P.falciparum*. This test, termed in vitro growth inhibition, was employed as a correlate of clinical protection produced by vaccination. In developing this procedure, human A positive erythrocytes, parasitized with the Indochina I strain of *P.falciparum* proteinaceous supernatant were cultured in the presence of normal human A positive serum, normal Saimiri serum, serum from animals vaccinated with soluble *P.falciparum* antigens in combination with adjuvant or animals that had been infected with parasitized erythrocytes. All immune sera were positive by the IFA test.

Immune Saimiri sera were diluted 1:2 with the normal Saimiri control sera. Complete RPMI 1640 medium containing 10% human serum, 10% normal Saimiri serum or 10% of each immune serum (1:20) was prepared. A 10% suspension of parasitized erythrocytes was prepared in each of the complete media and 0.5 ml of the suspension was added to duplicate or triplicate culture wells.

After erythrocytes settled, smears were made of all wells to obtain baseline percentage of parasitized erythrocytes. Tissue culture plates were incubated at 37° C. using a candle jar system, and each well was fed and smeared at 24 hour intervals up to 96 hours to determine percent parasitized erythrocytes.

C. Vaccination Procedures

A vaccination study was conducted using a total of four monkeys: susceptible negative control monkey; a preimmunized *P.falciparum* carrier monkey which recovered from the clinical disease about two months earlier; and two susceptible vaccinated monkeys (designated "vaccinate 1" and "vaccinate 2"). Vaccines were administered in two doses on days 2 and 23. During each vaccination period, the inoculum was divided into two equal volumes and each volume inoculated subcutaneously. In this fashion the primary dose was administered in the upper lateral thoracic region and the second dose was given in the lower lateral abdominal region of the recipient monkey.

The proteinaceous immunogen administered to vaccinate 1 was a 10× concentration of centrifuged, filtered and dialyzed mixtures of culture fluid medium supernatant and wash preparations of Example I. Vaccinate 2 received a 15× concentrated antigen. Negative and preimmunized control animals received normal culture supernatant and adjuvant in a like manner.

Prior to inoculation, equal volumes of concentrated antigen and Saponin (Quil-A) diluted 1:15 in PBS (pH 7.2) were admixed. The total vaccine volume used for each, primary and secondary inoculation, was 1.2 ml for vaccinate 1 and 2.0 ml for vaccinate 2. Negative and preimmunized control monkeys each received volumes of 1.2 ml of vaccine mixture on primary and secondary immunization.

Fifty-three days following primary inoculation, all four animals were challenged by i.v. administration (via saphenous vein) of $2.0 \times 10^7$ *P.falciparum* parasitized erythrocytes in balanced salt solution obtained from an acutely infected monkey.

Several days prior to vaccination and during post-vaccination and post-challenge periods, the rectal temperature of the animals and their clinical health were determined daily, while hematocrit levels and IFA determinations were made at intervals of approximately one week. Enumeration of the parasite in the peripheral blood samples was made microscopically using Giemsa-stained thick smears. In addition to the clinical protection, the evidence of protective immunity in vaccinated animals was revealed by active reticulocytosis using blood smears stained with new methylene blue, stable hematocrit levels, the pattern of IFA response following challenge, and the presence of structurally abnormal parasites situated intra- and extra-erythrocytically.

Animals which died were subjected to gross and histopathologic examination.

D. Results of Vaccination Tests

Humoral immune responses of test animals are graphically represented in FIG. 1. Both vaccinated monkeys developed a prompt humoral immune response as evidenced by the results of the IFA test. The maximum pre-challenge titer of the two monkeys was 1:163,840 and 1:10,000,000 at approximately 30 and 40 days respectively, following primary inoculation. After challenge (day 53 post-primary vaccine dose), an increase of the IFA titer was demonstrated in both vaccinated animals. The titer continued to rise and reached extremely high values 90 days post-challenge. With slight deviation, the titer of the carrier animal (positive control) followed a pattern similar to that of the vaccinated animals probably due to an immunomodulatory effect of the adjuvant. The negative control monkey developed a maximum titer of 1:20,480 approximately two weeks post-challenge and then declined by two serial serum dilutions prior to death.

Figure 9:
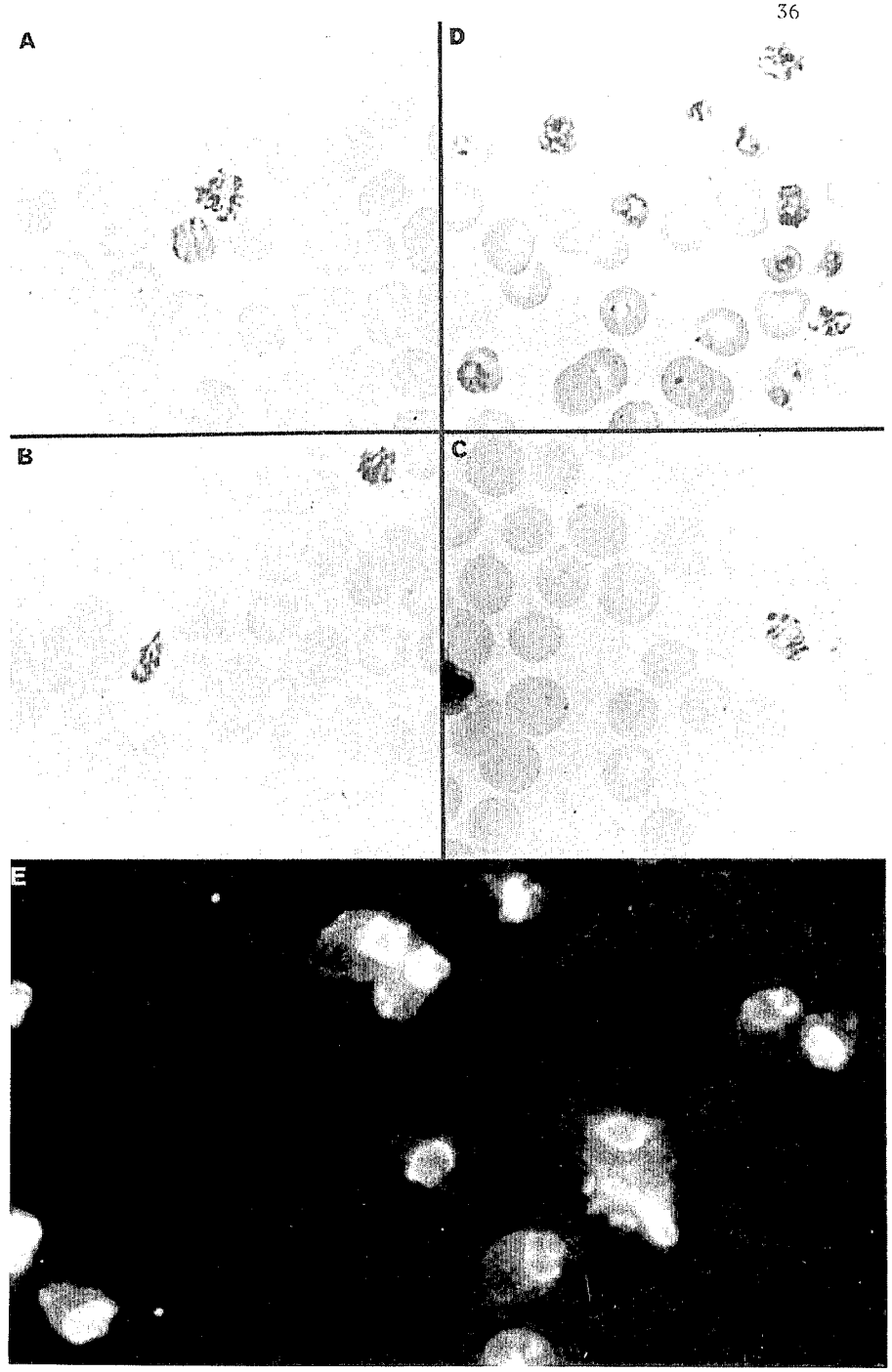

It is of interest to indicate that at serum dilutions between 1:10 and about 1:20,000 all organismal forms and, remarkably, the cytoplasm of infected cells showed prominent fluorescence. See FIG. 9, page E. The latter observation is indicative of the presence of soluble antigens in the cytoplasm. At higher serum dilutions, the fluorescence was mostly confined to the ring stage of the parasite.

Figure 2:
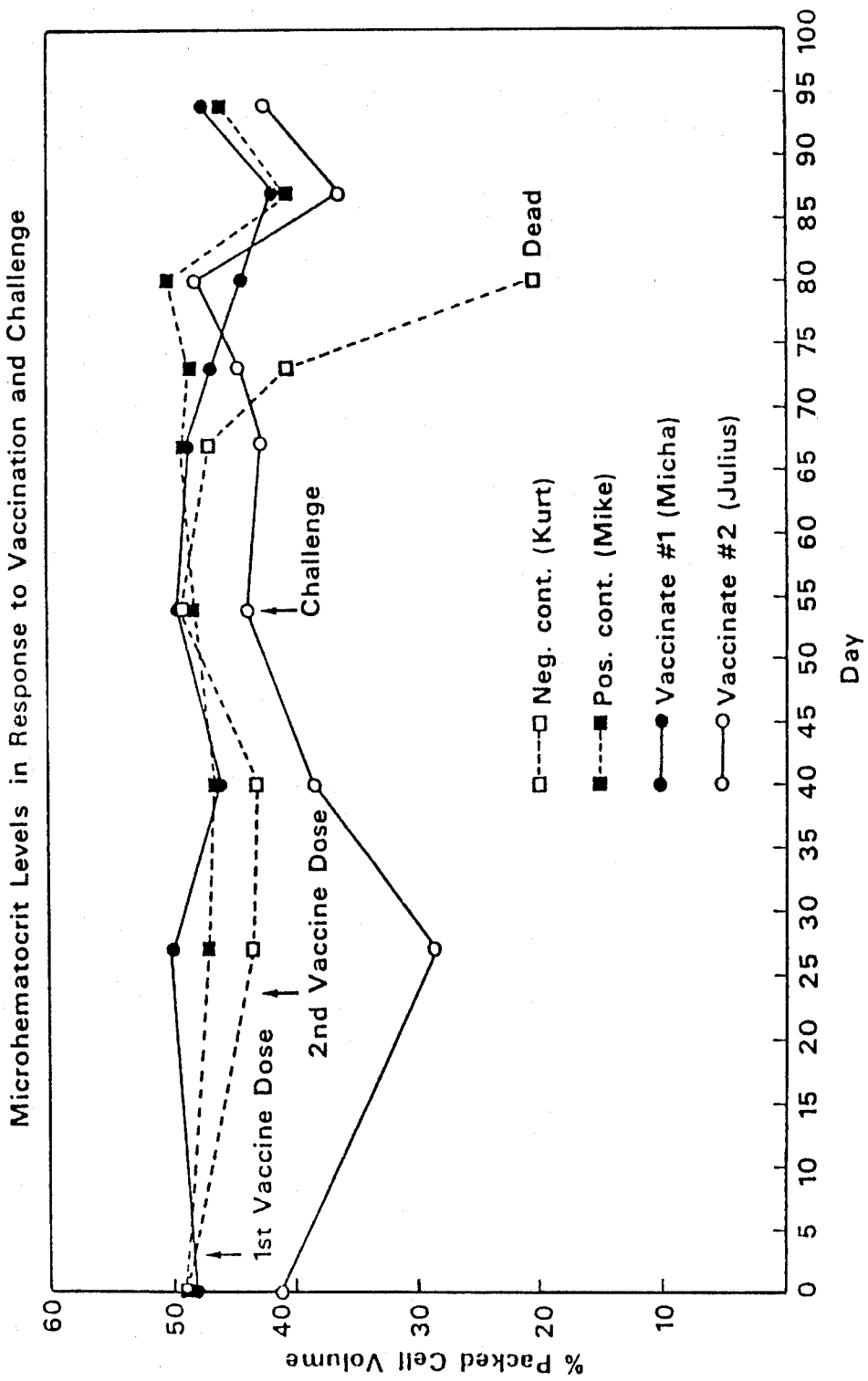

Hematocrit levels of test animals are graphically represented in FIG. 2. In general, the hematocrit levels of the two vaccinated animals and of the positive carrier control remained within normal range during the post-challenge period. Prior to challenge a total of three hematocrit examinations were made. Two of these examinations were made after the second vaccinal dose. A hematocrit decrease from 40% prior to vaccination to 30% shortly after the second vaccinal dose was noted in one of the vaccinated animals, possibly due to the saponin adjuvant dose. On the day of challenge, the hematocrit of this animal reached the equivalent prevaccination level of about 40%. The negative control monkey demonstrated a severe hematocrit decrease beginning on day 17 post-challenge, reaching a level of 20% on the day the animal died at 25 days post-challenge. Accordingly, challenge exposure resulted in approximately a 50% hematocrit decrease in the control animal.

Figure 3:
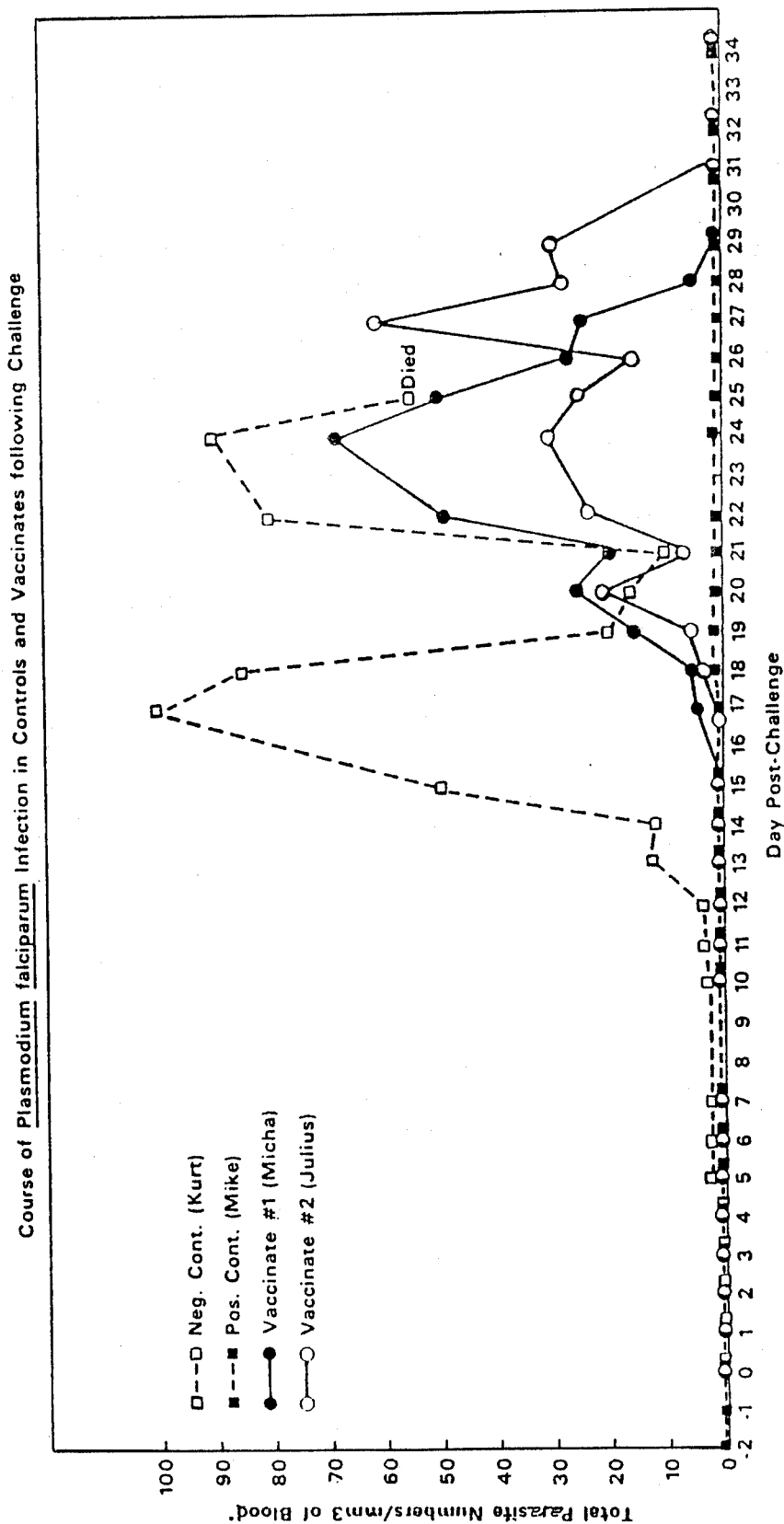
Figure 4:
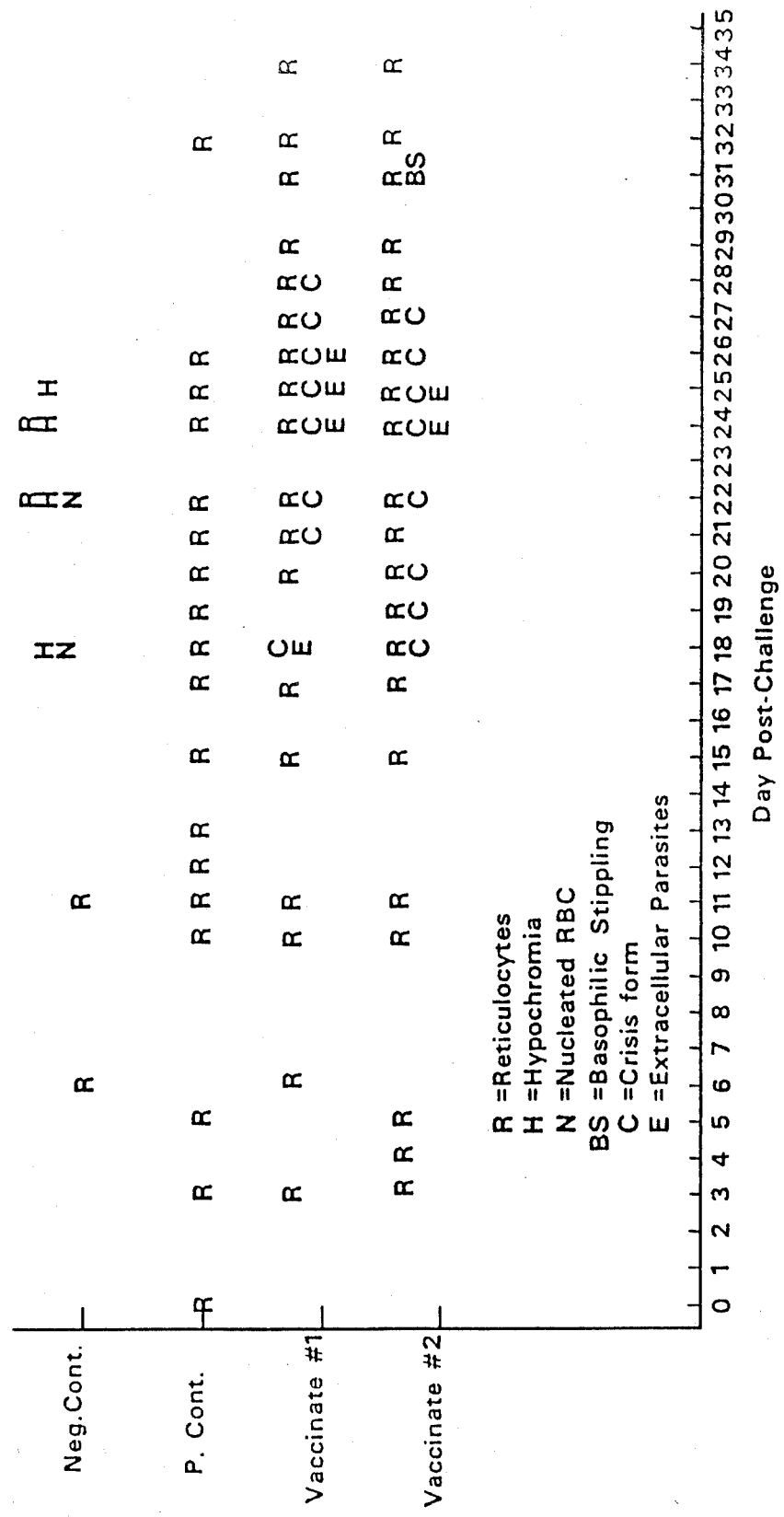

Parasitemias calculated on the basis of thick blood smear examination are expressed as the total parasite number/mm$^3$ of blood and are shown in FIG. 3. In the scale shown in FIG. 4 maximum parasite number (45,155 parasitized mm$^3$ blood) is equal to 100%. The negative control animal demonstrated two parasitemia peaks with 45,155 and 41,000 parasites/mm$^3$ of blood observed on days 17 and 24 post-challenge, respectively. During the majority of the post-challenge period prior to recovery, the parasitemia levels in vaccinates were only about 25% of that seen in the negative control with the exception of one reading period where parasitemia was about 50% of that seen in the negative control. Only negligible parasite numbers were detected in the positive control monkey.

Aside from the difference in parasitemias between vaccinates and the susceptible control, vaccinates exhibited a delayed prepatent period with parasites detectable on thin smears long after acute disease symptoms were observed in the control monkey.

Microscopic examination of the parasites in vaccinated animals using Giemsa-stained thin blood films showed that more than 50% of the parasites were structurally abnormal and that many of these were situated extracellularly. The presence of such abnormal parasite forms and the evidence of reticulocytosis in the vaccinates and the preimmunized control, along with other pertinent parameters during the post-challenge period are presented in FIG. 4. The presence of abnormal parasites was limited to the vaccinated animals only. Compare, for example, the Giesma-stained thin blood films of immunized monkeys in FIG. 9, plates A, B and C with that of blood from a non-vaccinated, splenectomized monkey shown in FIG. 9, plate D.

No clinical signs of the disease were observed in either the two vaccinated or the previously infected (preimmunized) monkey. Their feeding habits and general alertness and reflexes remained unchanged and their rectal temperatures were normal. The negative control monkey, however, developed a typical *P. falciparum* infection. During the parasitemia crisis the temperature of this animal reached 105.4° F., he appeared grossly anemic, with apparent signs of arthralgia. Shortly before death the animal developed anoxia, went into shock and expired.

EXAMPLE VII

This example relates to a vaccination study conducted using a single susceptible Saimiri monkey. The vaccine in this instance consisted of the 10x antigen as in Example VI, to which was added an aluminum hydroxide, rather than saponin, adjuvant. The animal was inoculated in the fashion described above with two vaccinal doses administered subcutaneously on days 0 (May, 1982) and 21 (June, 1982). The primary vaccinal dose consisted of 0.5 ml of antigen and 0.05 ml of adjuvant, while the second dose was prepared by admixing 0.4 ml of antigen and 0.15 of adjuvant. The maximal anti-schizont titer in this animal exceeded 1:10,480 and the anti-ring titer was greater still. High antiplasmoidal antibody titers were maintained for three months. By December, 1982, the titer had dropped to 1:10. This animal was challenged approximately 9 months after the primary vaccination as noted in the Example VIII procedure.

EXAMPLE VIII

This example relates to a second vaccination study involving a total of eight monkeys.

A. Animals, Analytical Procedures and Vaccination Procedures

All monkeys were handled as in Example VI. Of these eight animals, three were previously infected and thus known to be malarial carriers. These were included to assess the effects of vaccines of the invention on previously-infected patients who are common among the populations at highest risk of malarial infection. The remaining animals were Plasmodium-free, susceptible subjects Individual animals and treatment received may be listed as follows:

No. 1. (First Carrier)—Was immunized with a mixture of supernatant and wash antigen preparations from monkey cell cultures;

No. 2. (Second Carrier)—Was immunized with a mixture of supernatant and wash antigen preparations from human cell cultures;

No. 3. (Third Carrier)—Was immunized with a formalin-treated mixture of supernatant and wash antigen preparations from human cell cultures;

No. 4. (First Susceptible)—Was immunized about six months previously in the procedure of Example VII;

No. 5. (Second Susceptible)—Was immunized with a mixture of supernatant and wash antigen preparations from monkey cell cultures;

No. 6. (Third Susceptible)—Was immunized with a formalin-treated mixture of supernatant and wash antigen preparations from monkey cell cultures;

No. 7. (Fourth Susceptible)—Was immunized with a mixture of supernatant and wash antigen preparations from human cell cultures; and No. 8. (Fifth Susceptible)—Served as the non-immunized control and was inoculated with a mixture of supernatant and wash antigen preparations of uninfected monkey cells.

Prior to use, all antigens were concentrated 13 to 14 times. Formalin treatment of the antigen involved stirred mixing with a 0.5% solution of formalin at room temperature for 24 hours. Afterwards, the antigen/formalin mixture was dialyzed extensively against PBS at 4° C., pH 7.2, to remove formalin, and stored at −80° C. until use. Primary vaccinations consisted of 0.5 ml of antigen concentrate (about 25 mg protein) combined with 50 μl of aluminum hydroxide adjuvant (Alhydrogel) solution as in Example V. Second vaccinal doses consisted of 0.5 ml antigen concentrate with 150 μl adjuvant. All animals except No. 4 were given the primary inoculation on Dec. 20, 1982 (day 0 of study) and the second inoculation on Jan. 17, 1983 (day 28). On Feb. 16, 1983 (day 58), all animals were challenged by intravenous administration of a balanced salt solution containing approximately $1 \times 10^6$ *P.falciparum* (Indochina I) parasitized erythrocytes from an acutely infected monkey. Pre- and post-challenge analytical procedures and determinations of clinical information were carried out as in Example VI.

B. Results of Vaccination Tests

Humoral immune responses (IFA titers "S" for schizont, "R" for ring where differentials were conspicuous) and hematocrit levels of test animals in this vaccination study are set out in tabular form in Tables 4 through 11.

TABLE 4

Animal No: 1 (First Carrier)
Immunization Protocol: Wash and Supernatant Antigen, Monkey Cell Culture

| Procedure Day | IFA Titer | Hematocrit |
|---|---|---|
| −11 | — | 47.0 |
| −5 | 1:320 | — |
| −4 | — | 50.0 |
| 0 (Vaccination 1) | — | — |
| +9 | 1:160 | 45.0 |
| +18 | 1:640 | 47.1 |
| +25 | 1:160 | 50.0 |
| +28 (Vaccination 2) | — | — |
| +35 | 1:640 S | 48.4 |
| +42 | 1:640 | 45.9 |
| +49 | 1:1280 | 44.6 |
| +56 | 1:320 | 46.4 |
| +58 (Challenge) | — | — |
| +65 | 1:640 | 39.0 |
| +72 | 1:640 | 44.6 |
| +79 | 1:10,240 | 44.4 |
| +86 | 1:2,560 | 50.0 |
| +93 | 1:10,240 | 44.4 |
| +100 | 1:1,280 | 46.1 |
| +107 | 1:1,280 | 50.0 |
| +121 | 1:1,280 | — |
| +128 | 1:160 | — |

TABLE 5

Animal No: 2 (Second Carrier)
Immunization Protocol: Wash and Supernatant Antigen, Human Cell Culture

| Procedure Day | IFA Titer | Hematocrit |
|---|---|---|
| −11 | — | 48.0 |
| −5 | 1:10,240 | — |
| −4 | — | 49.0 |
| 0 (Vaccination 1) | — | — |
| +9 | 1:5,120 | 50.0 |
| +18 | 1:5,120 | 46.5 |
| +25 | 1:5,120 S | 45.0 |
|  | 1:655,320 R |  |
| +28 (Vaccination 2) | — | — |
| +35 | 1:640 S | 47.1 |
|  | 1:20,480 R |  |
| +42 | 1:1,280 S | 47.0 |
|  | 1:10,240 R |  |
| +49 | 1:10,240 | 43.2 |
| +56 | 1:655,320 | 47.5 |
| +58 (Challenge) | — | — |
| +65 | 1:2,560 | 43.0 |
| +72 | 1:5,120 | 47.5 |
| +79 | 1:10,240 | 48.0 |
| +86 | 1:10,240 | 48.1 |
| +93 | 1:5,120 | 47.0 |
| +100 | 1:2,560 | 46.5 |
| +107 | 1:2,560 | 46.0 |
| +121 | 1:2,560 | — |
| +128 | 1:1,280 | — |

TABLE 6

Animal No: 3 (Third Carrier)
Immunization Protocol: Formalin-treated Wash and Supernatant Antigen, Human Cell Culture

| Procedure Day | IFA Titer | Hematocrit |
|---|---|---|
| −11 | — | 44.0 |
| −5 | 1:320 | — |
| −4 | — | 45.0 |
| 0 (Vaccination 1) | — | — |
| +9 | 1:160 | 45.0 |
| +18 | 1:320 | 42.5 |
| +25 | 1:320 S | 48.3 |
|  | 1:1,280 R |  |
| +28 (Vaccination 2) | — | — |
| +35 | 1:1,280 | 46.3 |
| +42 | 1:1,280 | 46.6 |
| +49 | 1:2,560 | 44.0 |
| +56 | 1:20,480 | 43.1 |
| +58 (Challenge) | — | — |
| +65 | 1:640 | 41.0 |
| +72 | 1:640 | 44.8 |
| +79 | 1:10,240 | 45.2 |
| +86 | 1:10,240 | 48.2 |
| +93 | 1:2,560 | 47.9 |
| +100 | 1:5,120 | 45.5 |
| +107 | 1:10,240 | 47.3 |
| +121 | 1:2,560 | — |
| +128 | 1:1,280 | — |

TABLE 7

Animal No: 4 (First Susceptible)
Immunization Protocol: Supernatant Antigen, Monkey Cell Culture (See Example VII)

| Procedure Day | IFA Titer | Hematocrit |
|---|---|---|
| [Vaccinations 1 and 2 at −6 Months] | — | — |
| −11 | — | 46.0 |
| −5 | 1:20 | — |
| −4 | — | 44.0 |
| 0 | — | — |
| +9 | 1:20 | 47.0 |
| +18 | 1:40 | 46.7 |
| +25 | 1:20 | 45.4 |
| +28 | — | — |
| +35 | 1:20 | 46.8 |
| +42 | 1:20 | 45.7 |
| +49 | 1:10 | 43.1 |
| +56 | 1:10 | 43.1 |
| +58 (Challenge) | — | — |
| +65 | 1:40 | 41.0 |
| +72 | 1:2,560 | 42.9 |
| +79 | 1:5,120 | 40.0 |
| +86 | 1:20,480 | 38.0 |
| +93 | 1:10,240 | 40.0 |
| +100 | 1:2,560 | 43.8 |
| +107 | 1:5,120 | 45.0 |
| +121 | 1:320 | — |

TABLE 7-continued

Animal No: 4 (First Susceptible)
Immunization Protocol: Supernatant Antigen, Monkey Cell Culture (See Example VII)

| Procedure Day | IFA Titer | Hematocrit |
|---|---|---|
| +128 | 1:320 | — |

TABLE 8

Animal No: 5 (Second Susceptible)
Immunization Protocol: Wash and Supernatant Antigen, Monkey Cell Culture

| Procedure Day | IFA Titer | Hematocrit |
|---|---|---|
| −11 | — | 47.0 |
| −5 | Neg. | — |
| −4 | — | 46.0 |
| 0 (Vaccination 1) | — | — |
| +9 | 1:10 | 40.0 |
| +18 | 1:20 | 38.2 |
| +25 | 1:40 | 36.5 |
| +28 (Vaccination 2) | — | — |
| +35 | 1:20 | 44.8 |
| +42 | 1:40 | 45.3 |
| +49 | 1:40 | 46.2 |
| +56 | 1:40 | 47.6 |
| +58 (Challenge) | — | — |
| +65 | 1:1,280 | 42.0 |
| +72 | 1:1,280 | 41.2 |
| +79 | 1:5,120 | 38.0 |
| +86 | 1:2,560 | 44.0 |
| +93 | 1:2,560 | 46.1 |
| +100 | 1:640 | 48.0 |
| +107 | 1:1,280 | 46.1 |
| +121 | 1:640 | — |
| +128 | 1:320 | — |

TABLE 9

Animal No: 6 (Third Susceptible)
Immunization Protocol: Formalin-Treated Wash and Supernatant Antigen, Monkey Cell Culture

| Procedure Day | IFA Titer | Hematocrit |
|---|---|---|
| −11 | — | 51.0 |
| −5 | Neg. | — |
| −4 | — | 49.0 |
| 0 (Vaccination 1) | — | — |
| +9 | 1:10 | 52.0 |
| +18 | 1:20 | 48.0 |
| +25 | 1:40 | 48.6 |
| +28 (Vaccination 2) | — | — |
| +35 | 1:5,120 | 51.4 |
| +42 | 1:320 S<br>1:5,120 R | 47.1 |
| +49 | 1:1,280 | 48.5 |
| +56 | 1:20,480 | 48.1 |
| +58 (Challenge) | — | — |
| +65 | 1:320 | 46.0 |
| +72 | 1:640 | 48.5 |
| +79 | 1:20,480 | 20.0 |
| +86 | 1:10,240 | 31.6 |
| +93 | 1:5,120 | 42.4 |
| +100 | 1:1,280 | 48.1 |
| +107 | 1:640 | 47.2 |
| +121 | 1:640 | — |
| +128 | 1:640 | — |

TABLE 10

Animal No: 7 (Fourth Susceptible)
Immunization Protocol: Wash and Supernatant Antigen, Human Cell Culture

| Procedure Day | IFA Titer | Hematocrit |
|---|---|---|
| −9 | — | 47.0 |
| −5 | Neg. | — |
| −4 | — | 50.0 |
| 0 (Vaccination 1) | — | — |
| +9 | 1:20 | 50.0 |
| +18 | 1:80 | 48.0 |
| +25 | 1:320 | 44.4 |
| +28 (Vaccination 2) | — | — |
| +35 | 1:160 S<br>1:640 R | 47.4 |
| +42 | 1:320 | 46.8 |
| +49 | 1:1,280 | 47.3 |
| +56 | 1 20,480 | 46.7 |
| +58 (Challenge) | — | — |
| +65 | 1:640 | 44.0 |
| +72 | 1:1,280 | 37.7 |
| +79 | 1:10,240 | 31.4 |
| +86 | 1:20,480 | 42.3 |
| +93 | 1:5,120 | 46.7 |
| +100 | 1:1,280 | 47.5 |
| +107 | 1:2,560 | 47.5 |
| +121 | 1:160 | — |
| +128 | 1:320 | — |

TABLE 11

Animal No: 8 (Fifth Susceptible)
Immunization Protocol: Uninfected Monkey Cell Supernatant and Cell Wash

| Procedure Day | IFA Titer | Hematocrit |
|---|---|---|
| −11 | — | 45.0 |
| −5 | Neg. | — |
| −4 | — | 46.0 |
| 0 (Vaccination 1) | — | — |
| +9 | Neg | 50.0 |
| +18 | Neg. | 44.2 |
| +25 | Neg. | 44.3 |
| +28 (Vaccination 2) | — | — |
| +35 | Neg. | 45.8 |
| +42 | Neg. | 45.5 |
| +49 | Neg. | 48.0 |
| +56 | Neg. | 45.5 |
| +58 (Challenge) | — | — |
| +65 | Neg. | 43.0 |
| +72 | 1:40 | 47.6 |
| +79 | 1:80 | 36.8 |
| +86 | 1:320 | 13.2 |
| +93 | DEAD | DEAD |

Several aspects of the immunological data in the preceding Tables are noteworthy. Vaccinated animals which recorded appreciable IFA titer prior to challenge revealed a decrease in titer during the first post-challenge examination period (7 days post challenge). On the other hand, animals which had rather low antibody titer prior to challenge (e.g., Nos. 4 and 5) demonstrated a spontaneous rise in antibody titer at 7 days post-challenge. It can be postulated that in animals with an existing antibody titer there is an initial removal of antibodies by invading organism, followed by an increase in titer.

A comparison between No. 8 (control) and vaccinated animals revealed a marked difference in post-challenge antibody response. The maximal IFA antibody titer revealed by No. 8 was 1:320, while titers of vaccinated animals ranged from a low of 1:2560 to a high of 1:20,480. Calculated on an average antibody basis, vaccinated animals had a titer of 1:10,480.

The hematocrit levels of all animals post-vaccination and prior to challenge were stable. With the exception of No. 6, which had a single pronounced hematocrit decrease (20%) on day 21 post-challenge and showed a rapid recovery on the next examination period (31.6%), all other vaccinated animals retained a creditable hematocrit level through post-challenge periods. Hematocrit readings of Nos. 4 and 5 were nearly comparable with those of the three carrier animals (Nos. 1, 2 and 3). In contrast, No. 8 (negative control) developed a sudden decrease in hematocrit from 36.8% to 13.2% during a one-week period prior to death.

FIG. 8 sets out information concerning extent of post-challenge parasitemia in the eight experimental animals. Data concerning peak parasitemia correlated to time elapsed after challenge as determined by thin and thick blood smear procedures is set out in Table 12, below. While single parasites were occasionally seen in thin smears of carrier animals (Nos. 1, 2 and 3), parasitemia was considered to be "zero".

TABLE 12

| Animal No. | Peak Parasitemia (%) | Days Post-Challenge | |
|---|---|---|---|
| | | Thin | Thick |
| 1 | 0 | — | 20 |
| 2 | 0 | — | 26 |
| 3 | 0 | — | 15 |
| 4 | 0.6 | 19 | 26 |
| 5 | 1.7 | 20 | 15 |
| 6 | 5.6 | 19 | 19 |
| 7 | 4.9 | 13 | 14 |
| 8 | 27.0 | 29 | 29 |

This data is consistent with hematocrit and IFA titer data and indicates that vaccinated susceptible animals reached peak parasitemia in advance of the negative control animal.

Following primary and secondary vaccinations, neither the susceptible nor carrier of the animals showed any signs of immediate or delayed-type hypersensitivity. Also, there was no indication at the site of inoculation of any clinically detectable tissue damage. Following challenge, No. 8 was the only animal which developed typical signs of *P.falciparum* malaria, including fever spikes. These signs were most pronounced during a period of four to five days prior to death. During the last three days of his life, this animal developed a subnormal temperature ranging from $\leq 94°$ F. to 98° F. For most of this period the animal remained immobile on the perch or the floor of his cage and showed little or no response during handling and examination. The animal ceased to eat or drink two days prior to death on post-challenge day 29. Post-mortem examination of the animal revealed a multitude of the typical pathologic manifestations of acute malarial infection.

It is worthy of note that prior observations of Plasmodium infected animals reveal that two distinct shock syndromes are ordinarily experienced. The first is manifested by loss of equilibrium, abdominal contractions, dyspnea and sometimes a loss of consciousness from which the animal cannot be successfully resuscitated. This syndrome usually occurs during or just following crisis and has been observed repeatedly in Saimiri monkeys infected with *P.falciparum*, with animals having low hematocrit levels apparently being more prone to the syndrome. The second syndrome, which usually occurs after crisis and is not fatal, is characterized by epileptic-type seizures and paddling of the limbs. Neither shock syndrome was shown by any of the vaccinated Saimiri monkeys which were challenged with *P.falciparum* in the above studies.

EXAMPLE IX

Figure 5:
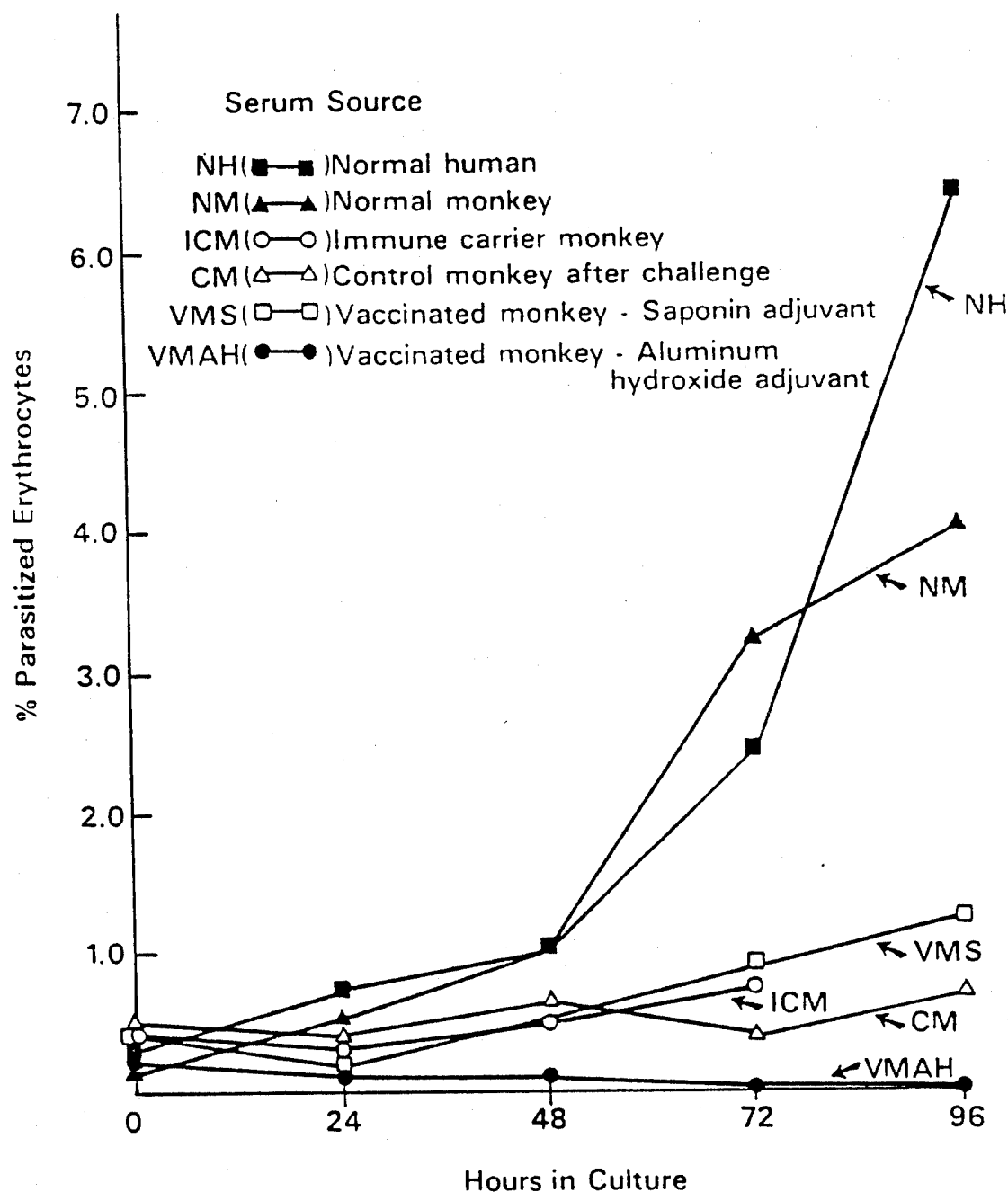

This example relates to in vitro growth inhibition of *P.falciparum* by immune Saimiri serum obtained from test animals in the previous Examples VI and VII. The results of these tests are set out in FIG. 5.

The most prominent and rapid inhibition of parasite reinvasion was achieved with the serum of the Example VII monkey immunized with soluble antigens fortified by the aluminum hydroxide adjuvant. The inhibiting anti-parasite antibody effect was well illustrated by the appearance of deformed and extra-cellularly-occuring parasites as revealed by microscopic examination of Giemsa-stained thin blood films. It should be noted that the serum antibody generated in Example VII reacted in double diffusion in gel with soluble antigen from human culture as discussed in Example IV(A).

Sera from infected monkeys and those animals vaccinated with Saponin and soluble antigen showed a similar degree of inhibition of reinvasion in comparison with normal human and monkey sera.

Another study was conducted to examine growth inhibition effects in a heterologous strain system. In this case, sera produced in response to vaccination with soluble supernatant antigens derived from cultures of *P.falciparum*, "Geneve" strain, which originated in the Senegal region of Northwest Africa. As indicated in FIG. 6, antiserum of a monkey vaccinated with the Indochina I strain supernatant antigen and aluminum hydroxide adjuvant (Example VII) showed a considerable degree of growth inhibition of the Geneve strain parasites in comparison to normal human and monkey sera, with growth inhibition characteristics being essentially on par with those of serum of a recovered carrier monkey previously infected with the Indochina I strain.

The foregoing Examples are believed to clearly illustrate numerous interrelated aspects of the present invention having to do with the in vitro propagation of plasmodial parasites and development of protective vaccines employing materials generated in the course of such propagation. The disclosures of Example 1 relating to "screening" procedures, when combined with subsequent disclosures of the consistent development of large populations of parasitized erythrocytes, illustrate that aspect of the invention which constitutes a substantial improvement in propagative procedures of the prior art. Whenever initial continuous cultured growth of parasites is effected by addition of infected erythrocytes to susceptible, uninfected erythrocytes in a medium including serum, practice of the invention dictates use of combinations of erythrocytes and serum from blood sources having the same blood group (saline reactive) antigens, and antigens reactive with atypical antibodies. In this manner, common antigen/antibody agglutination reactions are entirely avoided in both the initial cultures and all subsequent subcultures. Not only do these procedures immensely facilitate production and isolation of the soluble antigens employed in vaccines of the invention, they also make available large populations of late erythrocytic-stage parasites. Such parasitic forms, including schizonts and merozoites, may be advantageously employed to provide solubilized antigens such as those described in U.K. published Patent Application Nos. 2,096,893 and 2,099,300. Practice of the improved propagative methods of the present invention is thus seen to facilitate any attempt to isolate those insoluble antigenic materials which may be associated with plasmodial parasites and parasite fractions.

In another of its aspects, the present invention provides the first verified demonstration ever that in vitro cultivation of plasmodial parasites can consistently generate water-soluble antigenic materials which, upon isolation from culture medium supernatant and wash preparations, can generate in a vaccinated primate a protective immune response to a massive malarial parasite challenge. It is noteworthy that the protective effects of vaccination according to the invention are enduring in nature. Animal No. 4 of Example VIII was unequivocally protected against a lethal parasitic challenge despite the passage of seven months between vaccination and challenge and despite the decrease in level of circulating antimalarial antibodies to less than that commonly found in carrier animals. The development of such a long-term, anemnestic response has no counterpart in the decades of vaccination studies which preceded the present invention.

It will be apparent to those skilled in the art that numerous adjuvants may be employed in combination with antigens provided by the invention, including, but not limited to: surface active substances, e.g., hexadecylamine, octadecylamine, lysolecithin, dimethyldioctadecylammonium bromide, N,N-dioctadecyl-N'-N'-bis(2-hydroxyethyl-propanediamine), methoxyhexadecylglycerol, and pluronic polyols; polyanions, e.g., pyran, dectran sulfate, poly IC, polyacrylic acid, carbopol; peptides, e.g., muramyl dipeptide, dimethylglycine, tuftsin; oil emulsions; and alum. It is noteworthy, however, that protective effects in primates have been developed without resort to the use of adjuvant materials such as FCA or the like. Again, there is no precedent for the use in primates of safe adjuvants such as saponin and aluminum hydroxide to assist in generation of immune responses protective against lethal plasmodial challenges. Finally, the illustrative examples clearly establish that agents such as formalin can be employed to treat antigenic vaccine components without loss of immunogenic efficacy.

Unit doses of proteinaceous supernatant and wash-derived antigens employed in, e.g., Example VIII, consisted of about 25 mg of relatively impure supernatant and wash materials. Effective amounts of proteinaceous material for incorporation into unit dose vaccine formulations of the invention can thus be expected to vary widely depending to a large extent on the degree of purity of the one or more antigens employed and may consist of as little as about 0.1 mg as much as about 100 mg of proteinaceous culture-derived material.

The procedures of the above illustrative examples involve the use of Plasmodium falciparum parasites. They were designed to establish the closest possible analogy in test procedures to plasmodial infections in, and anti-plasmodial vaccination of, human beings. It will be understood, however, that the various methods and materials of the invention may be easily adapted to use with other human-specific plasmodial species including *P.vivax*, *P.ovale* and *P.malariae*, as well as with those species which are specific for non-human hosts.

Numerous modifications and variations in practice of the invention are therefore expected to occur to those skilled in the art upon consideration of the foregoing disclosures and illustrative examples of preferred embodiments. Consequently, only such limitations as presently appear in the appended claims should be placed upon the invention.

What is claimed is:

1. A vaccine composition for use in developing a protective immune response in a vertebrate animal susceptible to infection by *Plasmodium flaciparum* parasites, said composition comprising:
    (1) an immunologically effective amount of one or more water soluble proteinaceous immunogens having respective molecular weights within the range of about 35,000 and about 85,000, as determined by SDS-PAGE, produced in the course of the in vitro cultured growth and proliferation of *Plasmodium falciparum* parasites in a susceptible host erythrocyte cell culture and isolated from the host and parasite cell and cell fragment-free medium of such growth or host and parasite cell and cell fragment-free washes of infected host cells in such culture; and
    (2) an immunologically effective amount of immunologically acceptable carrier and adjuvant materials.

2. A vaccine composition according to claim 1 comprising one or both of two water soluble proteinaceous immunogens having respective molecular weights of about 42,000 and about 54,000.

3. A vaccine according to claim 1 wherein the susceptible erythrocytes are human erythrocytes.

4. A vaccine composition according to claim 1 wherein the immunologically acceptable adjuvant material is saponin.

5. A vaccine composition according to claim 1 wherein the immunologically acceptable adjuvant material is aluminum hydroxide.

6. A method for protecting a susceptible vertebrate against infection by *Plasmodium falciparum* parasites comprising administering a vaccine composition comprising:
    (1) an immunologically effective amount of one or more water soluble proteinaceous immunogens having respective molecular weights within the range of about 35,000 and about 85,000, as determined by SDS-PAGE, produced in the course of the in vitro cultured growth and proliferation of *Plasmodium falciparum* parasites in a susceptible host erythrocyte cell culture and isolated from the host and parasite cell and cell fragment-free medium of such growth or host and parasite cell and cell fragment-free washes of infected host cells in such culture; and
    (2) an immunologically effective amount of immunologically acceptable carrier and adjuvant materials.

* * * * *